United States Patent

Mantell et al.

(10) Patent No.: US 6,525,032 B2
(45) Date of Patent: Feb. 25, 2003

(54) PURINE DERIVATIVES

(75) Inventors: Simon John Mantell, County of Kent (GB); Sandra Marina Monaghan, County of Kent (GB); Peter Thomas Stephenson, County of Kent (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/789,236

(22) Filed: Feb. 20, 2001

(65) Prior Publication Data

US 2001/0020089 A1 Sep. 6, 2001

Related U.S. Application Data

(63) Continuation of application No. PCT/IB01/00167, filed on Feb. 9, 2001.
(60) Provisional application No. 60/188,648, filed on Mar. 10, 2000.

(30) Foreign Application Priority Data

Feb. 18, 2000  (GB) ............................................. 0003960

(51) Int. Cl.$^7$ .......................... A61K 31/70; C07H 19/00
(52) U.S. Cl. .......................... 514/45; 514/45; 536/26.7; 536/27.6; 536/27.61; 536/27.62
(58) Field of Search ..................... 514/45, 46; 536/26.7, 536/27.6, 27.61, 27.62

(56) References Cited

U.S. PATENT DOCUMENTS

| 5,140,015 A | 8/1992 | Olsson et al. .................. 514/46 |
| 5,593,975 A | 1/1997 | Cristalli ........................ 514/46 |

FOREIGN PATENT DOCUMENTS

| EP | 0488336 | 10/1995 | ......... C07H/19/167 |
| WO | 0023457 | 4/2000 | ......... C07H/19/167 |
| WO | 0077018 | 12/2000 | ........... C07H/19/00 |
| WO | 012130 | 4/2001 | ......... C07H/19/167 |
| WO | 0127131 | 4/2001 | ......... C07H/19/167 |

OTHER PUBLICATIONS

*J. Amer. chem. Soc.,* 80, p. 5168 (1958) and.
Berge, et al., *J. Pharm. sci.,* 66, pp. 1–19 (1977).

Primary Examiner—James O. Wilson
(74) Attorney, Agent, or Firm—Peter C. Richardson; Gregg C. Benson; Robert T. Ronau

(57) ABSTRACT

The present invention relates to compounds of the class of purin-2-ylcarboxamides, useful as anti-inflammatory agents, having the formula:

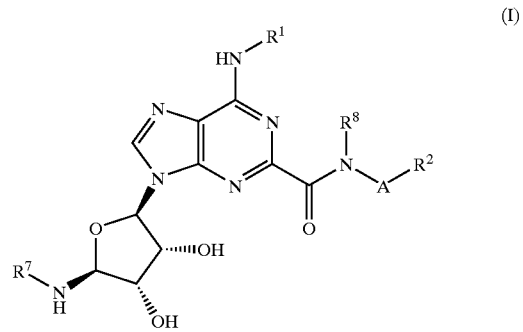

and pharmaceutically acceptable salts and solvates thereof; wherein $R^1$ is H, $C_1$–$C_6$ alkyl or $C_3$–$C_7$ cycloalkyl, each optionally substituted by 1 or 2 of hydroxyl, fluorenyl, or optionally substituted phenyl or naphthyl ; A is a bond or $C_1$–$C_6$ alkylene; $R^2$ is (i) H, $C_1$–$C_6$ alkyl, or optionally substituted $C_3$–$C_7$ cycloalkyl, phenyl, or naphthyl; or (ii) when A is $C_2$–$C_6$ alkylene, —$NR^3R^3$, —$OR^3$, —$COOR^3$, —$OCOR^4$, —$SO_2R^4$, —CN, —$SO_2NR^3R^4$, —$NR^3SO_2R^4$, —$NR^3COR^4$ or —$CONR^3R^3$; or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, said heterocycle being optionally C-substituted or N-substituted; or (iv) when A is $C_2$–$C_6$ alkylene, optionally substituted N-linked azetidinyl, pyrrolidinyl, morpholinyl, tetrahydroisoquinolinyl, piperidinyl or piperazinyl; $R^7$ is H, $C_1$–$C_6$ alkyl, $C_3$–$C_7$ cycloalkyl, phenyl, naphthyl, azetidin-3-yl, pyrrolidin-3-yl, piperidin-3-yl, piperidin-4-yl, or het; and $R^8$ is H or $C_1$–$C_6$ alkyl; and to intermediates used in processes for the preparation of, compositions containing, and uses as adenosine A2a receptor agonists of, compounds of formula (I).

11 Claims, No Drawings

PURINE DERIVATIVES

This application is a continuation of copending prior filed international application designating the U.S. Ser. No. PCT/IB01/00167 filed Feb. 9, 2001, the benefit of the filing date of which is claimed, and which is incorporated herein by reference in its entirety; corresponds to copending prior filed foreign application Great Britain Serial No. 0003960.2 filed Feb. 18, 2000, the benefit of the filing date of which is claimed, and which is incorporated herein by reference in its entirety; and is a continuation of prior filed provisional application U.S. Ser. No. 60/188,648 filed Mar. 10, 2000, the benefit of the filing date of which is claimed, and which is incorporated herein by reference in its entirety.

The present invention relates to certain purine derivatives. More particularly, the present invention relates to purin-2-ylcarboxamide derivatives, to their preparation, and to compositions, uses and intermediates used in the preparation thereof. These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, such as superoxide anion radicals ($O_2^-$), and granule products, such as human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2^-$ and HNE adversely affect pulmonary extracellular matrix. The A2 receptor subtype mediating many of these responses ($O_2^-$ and LTB4/HNE release and cell adhesion) is established as A2a. The A2 subtype (A2a or A2b) mediating the other effects remains to be established.

Selective agonist activity at the A2a receptor is considered to offer greater therapeutic benefit than non-selective adenosine receptor agonists because interaction with other receptor subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with a respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over this receptor is also advantageous.

We have now surprisingly found the present purine derivatives inhibit neutrophil function and are selective agonists of the adenosine A2a receptor.

The present compounds may be used to treat any disease for which an adenosine A2a receptor agonist is indicated. They can be used to treat a disease where leukocyte (e.g. neutrophil, eosinophil, basophil, lymphocyte, macrophage)—induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, Heliobacter pylori-gastritis, non-Heliobacter pylon gastritis, non-steroidal anti-inflammatory drug-induced damage to the gastro-intestinal tract or a psychotic disorder, or for wound healing.

Accordingly, in one aspect the present invention provides a compound of the formula:

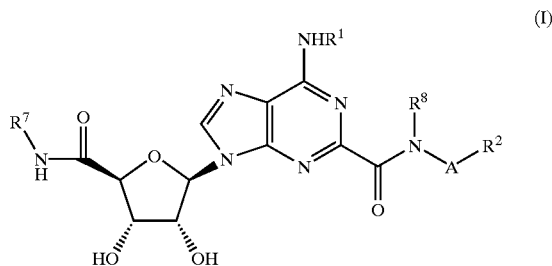

or a pharmaceutically acceptable salt or solvate thereof, wherein $R^1$ is hydrogen, $C_1$–$C_6$ alkyl or $C_3$–$C_7$ cycloalkyl, each optionally substituted by 1 or 2 substituents each independently selected from hydroxyl, fluorenyl, phenyl and naphthyl, said phenyl and naphthyl being optionally substituted by $C_1$–$C_6$ alkyl, $C_1$–$C_6$ alkoxy, halo or cyano;

A is a bond or $C_1$–$C_6$ alkylene;

$R^2$ is (i) hydrogen, $C_1$–$C_6$ alkyl, $C_3$–$C_7$ cycloalkyl, phenyl or naphthyl, said $C_3$–$C_7$ cycloalkyl, phenyl and naphthyl being optionally substituted by $C_1$–$C_6$ alkyl, phenyl, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_mR^4$, —$NR^3R^3$, —$SO_2NR^3R^3$, —$CONR^3R^3$, —$NR^3COR^4$ or —$NR^3SO_2R^4$, with the proviso that $R^2$ is not hydrogen when A is a bond, or (ii) when A is $C_2$–$C_6$ alkylene, —$NR^3R^3$, —$OR^3$, —$COOR^3$, —$OCOR^4$, —$SO_2R^4$, —CN, —$SO_2NR^3R^3$, —$NR^3SO_2R^4$, —$NR^3COR^4$ or —$CONR^3R^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, fluoro-($C_2$–$C_5$)-alkanoyl, halo, cyano, —$OR^5$, $R^6$, —$COR^5$, —$NR^5R^5$, —$COOR^5$, —$S(O)^mR^6$, —$SO_2NR^5R^5$, —$CONR^5R^5$, —$NR^5SO_2R^6$ or —$NR^5COR^6$ and optionally N-substituted by $C_1$–$C_6$ alkoxy-($C_1$–$C_6$)-alkyl, amino-($C_2$–$C_6$)-alkyl, fluoro-($C_1$–$C_6$)-alkyl, fluoro-($C_2$–$C_5$)-alkanoyl, $R^6$, —$COR^5$, —$COOR^6$, —$SO_2R^6$, —$SO_2NR^5R^5$ or —$CONR^5R^5$, or (iv) when A is $C_2$–$C_6$ alkylene, N-linked azetidinyl, pyrrolidinyl, morpholinyl, tetrahydroisoquinolinyl, piperidinyl or piperazinyl, each being optionally C-substituted by $C_1$–$C_6$ alkyl, phenyl, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_m R^4$, —$NR^3 R^3$, —$SO_2 NR^3 R^3$, —$CONR^3 R^3$, —$NR^3 COR^4$ or —$NR^3 SO_2 R^4$ and said piperazinyl being optionally N-substituted by $C_1$–$C_6$ alkyl, phenyl, $C_1$–$C_6$ alkoxy-($C_1$–$C_6$)-alkyl, amino-($C_2$–$C_6$)-alkyl, fluoro-($C_1$–$C_6$)-alkyl, $C_2$–$C_5$ alkanoyl, —$COOR^4$, $C_3$–$C_7$ cycloalkyl, —$SO_2 R^4$, —$SO_2 NR^3 R^3$ or —$CONR^3 R^3$;

each $R^3$ is independently selected from H, $C_1$–$C_6$ alkyl, phenyl or pyridinyl;

$R^4$ is $C_1$–$C_6$ alkyl or phenyl;

$R^5$ is H, $C_1$–$C_6$ alkyl, $C_3$–$C_7$ cycloalkyl, phenyl, naphthyl or het;

$R^6$ is $C_1$–$C_6$ alkyl, $C_3$–$C_7$ cycloalkyl, phenyl, naphthyl or het;

m is 0, 1 or 2;

$R^7$ is hydrogen, $C_1$–$C_6$ alkyl, $C_3$–$C_7$ cycloalkyl, phenyl, naphthyl, azetidin-3-yl, pyrrolidin-3-yl, piperidin-3-yl, piperidin-4-yl or het, said azetidin-3-yl, pyrrolidin-3-yl, piperidin-3-yl and piperidin-4-yl being optionally substituted by $C_1$–$C_6$ alkyl;

$R^8$ is H or $C_1$–$C_6$ alkyl; and

"het", used in the definitions of $R^5$, $R^6$ and $R^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each being optionally substituted by $C_1$–$C_6$ alkyl, $C_1$–$C_6$ alkoxy, cyano or halo.

Preferably, $R^1$ is cyclohexyl or optionally substituted $C_1$–$C_6$ alkyl. More preferably, $R^1$ is optionally substituted $C_1$–$C_5$ alkyl, and most preferably $R^1$ is optionally substituted $C_1$–$C_2$ alkyl. Preferably, the $C_1$–$C_6$, $C_1$–$C_5$, or $C_1$–$C_2$ alkyl substitutents are selected from benzyl, fluorenyl, phenyl and hydroxyl. Preferably, when $R^1$ is substituted by phenyl there are 1 or 2 phenyl group(s). Preferably, $R^1$ is selected from 2,2-diphenylethyl, cyclohexyl,1-ethylpropyl, 1-benzyl-2-hydroxyethyl, 9H-fluoren-9-ylmethyl, and 1-benzyl-2-phenylethyl. Preferably, $R^1$ is 2,2-diphenylethyl. Preferably, A is $C_1$–$C_6$ alkylene. Preferably, A is $C_1$–$C_4$ alkylene. Preferably, A is selected from methylene, 1,2-ethylene, 1,3-propylene, and 1,4-butylene. Preferably, A is 1,2-ethylene. Preferably, $R^2$ is selected from phenyl, pyrrolidinyl, pyridinyl, optionally substituted piperidinyl, optionally substituted piperazinyl, optionally substituted imidazolyl, morpholinyl, tetrahydroisoquinolyl, $C_1$–$C_6$ alkylamino, di- $C_1$–$C_6$ alkylamino, pyridinylamino, and —$NR^3 SO_2 R^4$. Preferably, $R^2$ is selected from phenyl, 2-pyridinyl, 1-piperazinyl, 4-piperidinyl, 1-pyrrolidinyl, 4-morpholinyl, 3,4-tetrahydro-2(1H)-isoquinolinyl, $C_1$–$C_3$ alkylamino, di- $C_1$–$C_3$ alkylamino, and substituted 1H-imidazol-4-yl.

Preferably, $R^2$ is selected from isopropylamino, methylamino, dimethylamino, diethylamino, 1-methyl-1H-imidazol-4-yl, 5-methyl-1H-imidazol-4-yl, 4-methylpiperazin-1-yl, 1-(2-propyl)piperidin-4-yl and 2-pyridylamino. Preferably, $R^2$ is piperidinyl optionally substituted by $C_1$–$C_6$ alkyl or methoxy. Preferably, $R^2$ is piperidinyl optionally substituted in the 1-position or 4-position by $C_1$–$C_6$ alkyl or methoxy. Preferably, $R^2$ is N-linked piperidinyl optionally C-substituted by $C_1$–$C_6$ alkyl or methoxy. Preferably, $R^2$ is N-linked piperidinyl optionally C-substituted by $C_1$–$C_3$ alkyl or methoxy.

Preferably, $R^2$ is N-linked piperidinyl optionally C-substituted by methyl, methoxy or propyl. Preferably, $R^2$ is N-linked piperidinyl optionally substituted in the 4-position by methyl, methoxy or propyl. Preferably, $R^2$ is piperidin-1-yl, 4-(methyl)piperidin-1-yl, 4-(methoxy)piperidin-1-yl or 4-(prop-2-yl)piperidin-1-yl.

Preferably, $R^3$ is methyl.

Preferably, $R^4$ is methyl or phenyl.

Preferably, $R^7$ is $C_1$–$C_6$ alkyl.

Preferably, $R^7$ is $C_1$–$C_4$ alkyl.

Preferably, $R^7$ is ethyl or n-propyl.

Preferably, $R^8$ is H.

In another aspect of the present invention, there is provided a compound of the formula (II), (III), (XI), (XIII), (XIV), (XV), (XVI), (XIX), (XIXb), (XIXc), or (XIXd):

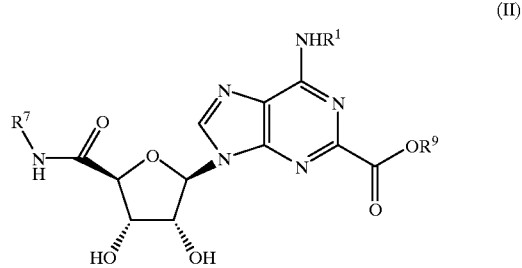

(II)

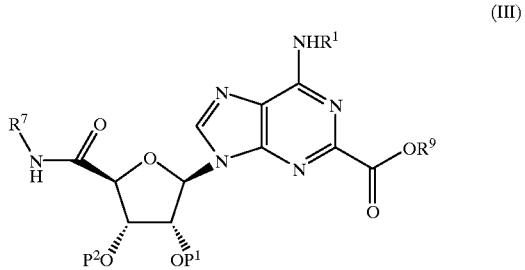

(III)

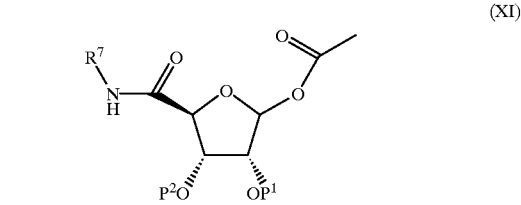

(XI)

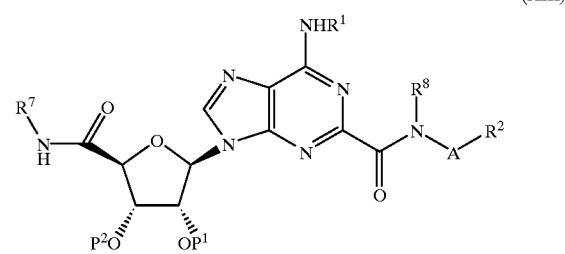

(XIII)

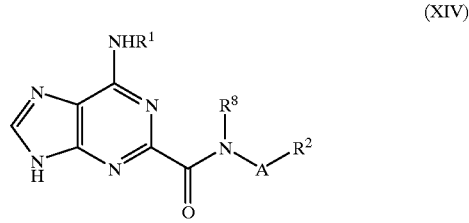

(XIV)

-continued (XV)
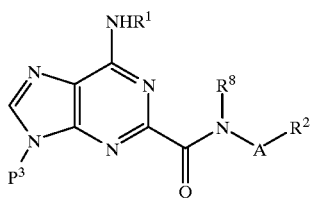

(XVI)
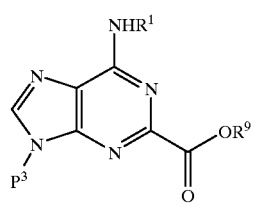

(XIX)
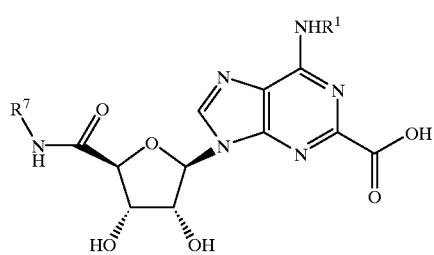

(XIXb)
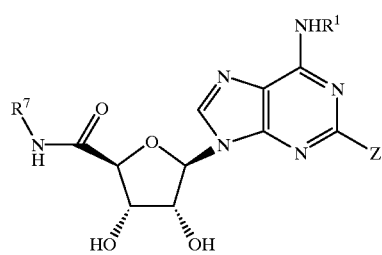

(XIXc)
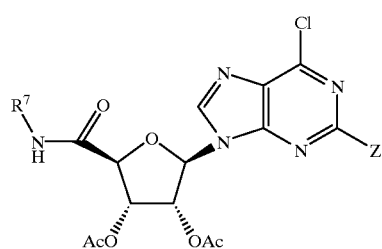

(XIXd)
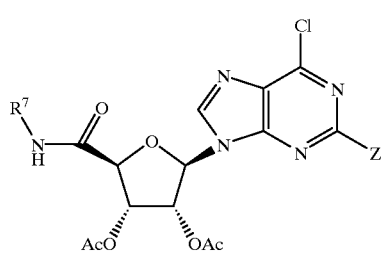

wherein $R^1$ to $R^8$, A, "het", and m when present are as defined above; $P^1$, $P^2$, and $P^3$ are protecting groups; and Z is a leaving group.

In another aspect of the present invention, there is provided a process for the preparation of a compound of formula (I), or a pharmaceutically acceptable salt thereof, the process comprising the step of reacting an ester of formula (II):

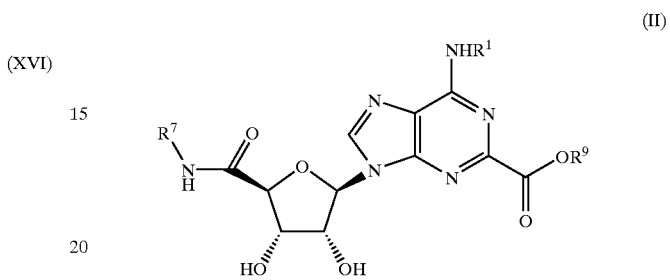

(II)

with an amine of the formula $R^2$-A-$NHR^8$ (X), wherein $R^1$ to $R^8$, A, "het" and m when present are as defined above.

In another aspect of the present invention, there is provided a process for the preparation of a compound of the formula (II):

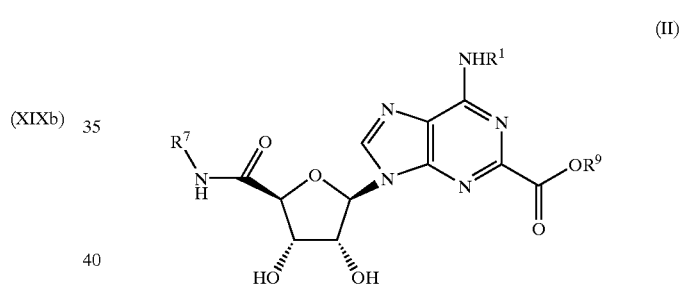

(II)

the process comprising the step of deprotecting a compound of formula (III):

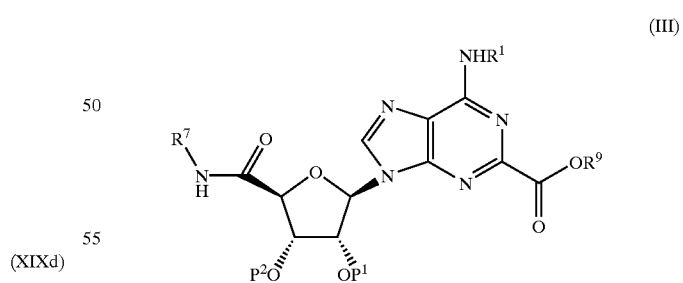

(III)

wherein $P^1$ and $P^2$ are protecting groups which may be the same or different or may be part of the same protecting group, and wherein $R^1$ to $R^8$, A, "het", and in when present are as defined above.

In another aspect of the present invention, there is provided a process for the preparation of a compound of the formula (III):

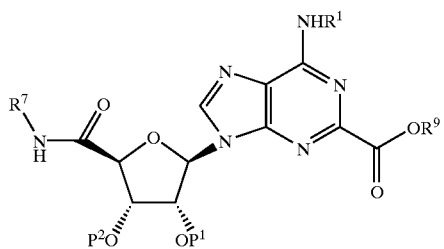

(III)

the process comprising the step of reacting a compound of the formula (XI):

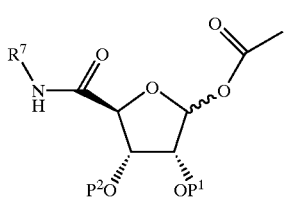

(XI)

wherein $P^1$ and $P^2$ are protecting groups with trimethylsilyltrifluoromethanesulfonate and a compound of the formula (IV):

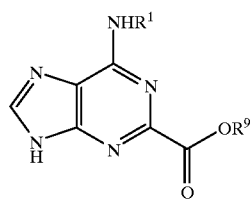

(IV)

wherein the compound of formula (IV) is derivatised with N,O-bis(trimethylsilyl) acetamide and then reacted with the compound of formula (XI), and wherein $R^1$ to $R^8$, A, "het", and m when present are as defined above.

In another aspect of the present invention, there is provided a process for the preparation of a compound of formula (IV):

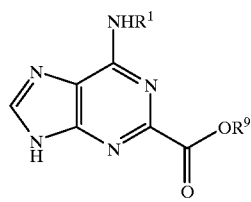

(IV)

by the alcoholysis and subsequent hydrolysis of a nitrile of formula (V):

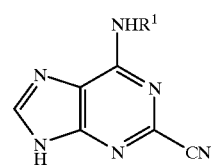

(V)

wherein $R^1$ is $R^8$, A, "het", and m when present are as defined above.

In another aspect of the present invention, there is provided a process for the preparation of a compound of the formula (V):

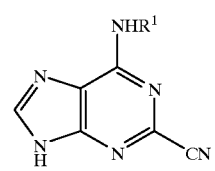

(V)

by the deprotection of a compound of formula (VI):

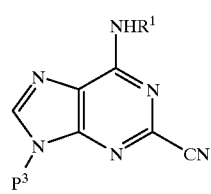

(VI)

wherein $P^3$ is a protecting group, and $R^1$ to $R^8$, A "het", and m when present are as defined above.

In another aspect of the present invention, there is provided a process for the preparation of a compound of the formula (VI):

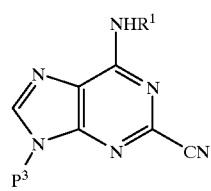

(VI)

by substitution of the chloro group in a compound of the formula (VII):

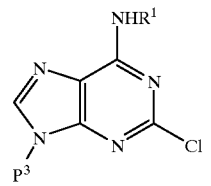

(VII)

with a cyano group, wherein $R^1$ is $R^8$, A, "het", and m when present are as defined above.

In another aspect of the present invention, there is provided a process for the preparation of a compound of the formula (VII):

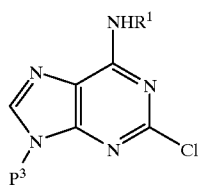

(VII)

by reaction of a compound of formula (VIII):

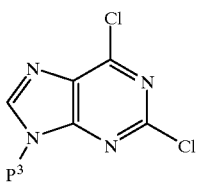

(VIII)

with an amino of formula $R^1NH_2$ (XII), wherein $R^1$ to $R^8$, A, "het", and m when present are as defined above.

In another aspect of the present invention, there is provided a process for the preparation of the a compound of the formula (VIII):

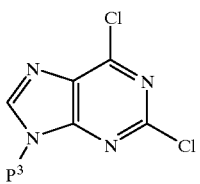

(VIII)

by the protection of 2,6-dichloro-9H-purine (IX):

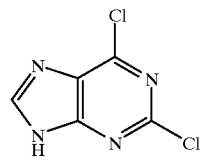

(IX)

In the above definitions, halo means fluoro, chloro, bromo or iodo and alkyl, alkylene, alkanoyl and alkoxy groups containing the requisite number of carbon atoms can be unbranched or branched chain. The heterocycle as defined in $R^2$, part (iii), above may be aromatic or fully or partially saturated. The expression 'C-linked' used in the definitions of $R^2$ and het means that the group is linked to the adjacent atom by a ring carbon. The expression 'N-linked' used in the definitions of $R^2$ means that the group is linked to the adjacent atom by a ring nitrogen. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl.

The pharmaceutically acceptable salts of the compounds of the formula (I) include the acid addition and the base salts thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and palmoate salts.

Suitable base salts are formed from bases which form non-toxic salts and examples are the sodium, potassium, aluminium, calcium, magnesium, zinc and diethanolamine salts.

For a review on suitable salts see Berge et al, *J. Pharm. Sci.*, 1977, 66, 1–19.

The pharmaceutically acceptable solvates of the compounds of the formula (I) include the hydrates thereof.

Also included within the present scope of the compounds of the formula (I) are polymorphs thereof.

A compound of the formula (I) may contain one or more additional asymmetric carbon atoms and therefore exist in two or more stereoisomeric forms. The present invention includes the individual stereoisomers of the compounds of the formula (I) together with mixtures thereof together, where appropriate, with the individual tautomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All the compounds of the formula (I) can be prepared by conventional routes such as by the procedures described in the general methods presented below or by the specific methods described in the Examples section, or by similar methods thereto. The present invention also encompasses any one or more of these processes for preparing the compounds of formula (I), in addition to any novel intermediates used therein. In the general methods described, $R^1$, $R^2$, $R^7$, $R^8$ and A are as previously defined for a compound of the formula (I) unless otherwise stated.

All the compounds of the formula (I) can be prepared according to the route shown in Scheme 1, wherein $R^9$ is $C_1$–$C_4$ alkyl, preferably methyl or ethyl, and $P^1$, $P^2$ and $P^3$ represent protecting groups.

Scheme 1

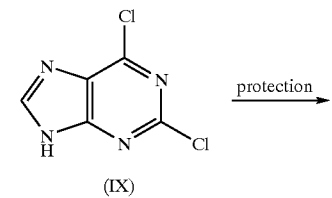

(IX)

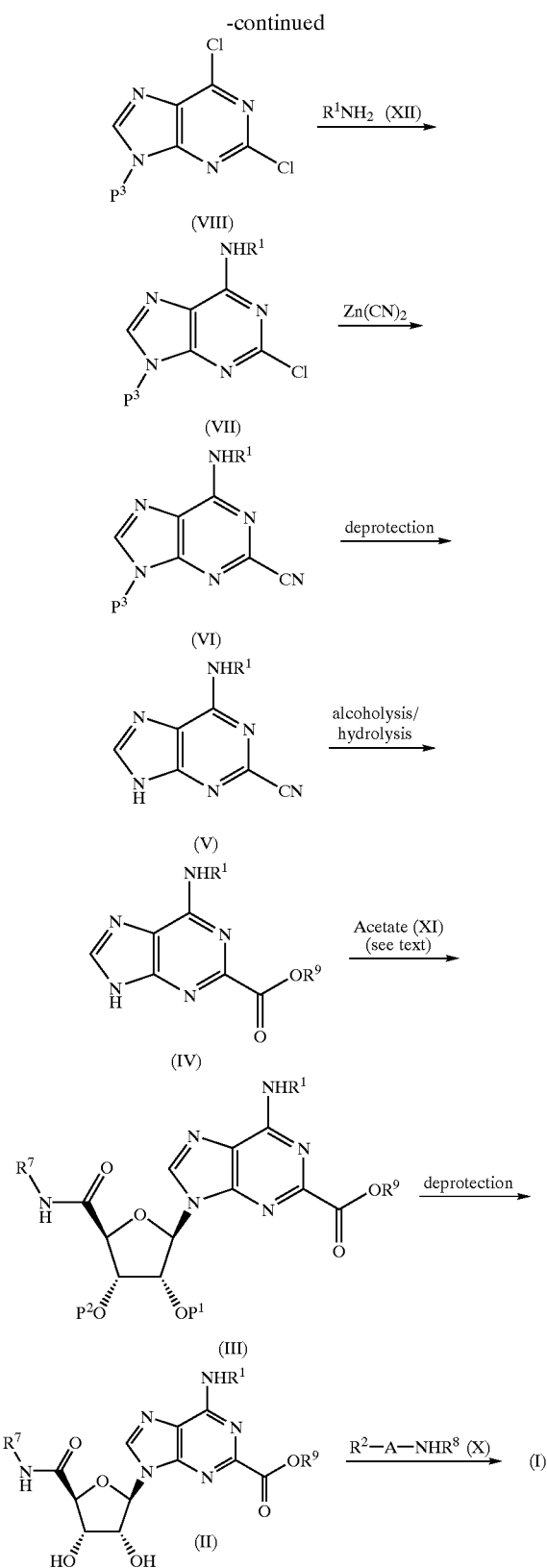

In Scheme 1, the compounds of the formula (I) may be prepared by reaction of an ester of the formula (II) with an amine of the formula

R²-A-NHR⁸      (X).

The reaction may be carried out at an elevated temperature, preferably from 100 to 150° C. and optionally in the presence of a suitable solvent such as ethanol. In a typical procedure, the compound of the formula (II) and the amine of the formula (X) are heated together at about 120° C. Compounds of formula (II) may be prepared by deprotection of a compound of the formula (III) wherein protecting groups $P^1$ and $P^2$ may be the same or different and may optionally form part of the same protecting group. Examples of suitable protecting groups will be apparent to the skilled person [see for instance 'Protecting Groups in Organic Synthesis (Second Edition)', Theodora W. Green and Peter G. M. Wuts, John Wiley and Sons, 1991]. Preferred individual protecting groups are alkanoyl and aroyl. Preferred protecting groups where $P^1$ and $P^2$ form part of the same protecting group are where $P^1$ and $P^2$ taken together are $C_1$–$C_6$ alkylene. Particularly preferred individual protecting groups are acetyl and benzoyl. A particularly preferred protecting group where $P^1$ and $P^2$ form part of the same protecting group is when $P^1$ and $P^2$ taken together are dimethylmethylene. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are each benzoyl, the protecting groups may be removed by treating a solution of the compound of the formula (III) in a suitable solvent, such as methanol, with a base such as potassium carbonate, typically at room temperature. Compounds of the formula (III) may be prepared by reaction of a compound of the formula (XI):

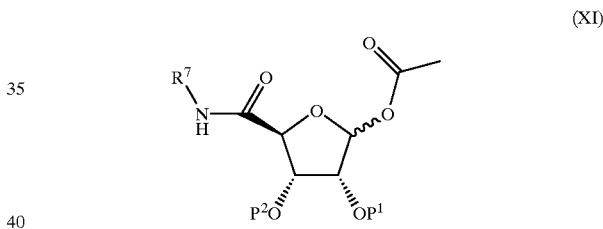

(in which $P^1$ and $P^2$ are as defined above) with trimethylsilyl trifluoromethanesulfonate and a compound of the formula (IV) which has been derivatised with N,O-bis(trimethylsilyl) acetamide. In a typical procedure, the compound of the formula (IV) is heated in the presence of a suitable solvent, such as 1,1,1-trichloroethane, and N,O-bis(trimethylsilyl) acetamide at an elevated temperature, preferably under reflux. The mixture is then allowed to cool and the solvent is removed. The residue is treated with a solution of the compound of the formula (XI) in a suitable solvent such as toluene, followed by trimethylsilyl trifluoromethanesulfonate and the mixture is heated under a nitrogen atmosphere at a temperature between room temperature and the reflux temperature of the chosen solvent to give the compound of the formula (III). In the case of toluene, for example, a temperature of 110° C. is preferred. Compounds of the formula (IV) may be prepared by a sequence of alcoholysis and hydrolysis applied to a nitrile of the formula (V). In a typical procedure, a solution of the nitrile of the formula (V) in an alcoholic solvent $R^9OH$ is treated a sodium alkoxide of the formula $R^9ONa$ and heated under reflux ($R^9$ is as defined above). The resulting mixture is cooled, evaporated, dissolved in a suitable solvent such as tetrahydrofuran and treated with an acid such as hydrochloric acid, preferably 2N hydrochloric acid, to give a compound of the formula (IV). Compounds of the formula (V)

may be prepared by deprotection of a compound of the formula (VI) wherein P³ is a suitable protecting group. Examples of suitable protecting groups will be apparent to the skilled person [see for instance 'Protecting Groups in Organic Synthesis (Second Edition)', Theodora W. Green and Peter G. M. Wuts, John Wiley and Sons, 1991]. A preferred protecting group is that in which P³ represents tetrahydropyran-2-yl. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where P³ is tetrahydropyran-2-yl, the protecting group may be removed by treating a solution of the compound of the formula (VI) in a suitable solvent, such as ethanol, with an acid such as hydrochloric acid. Compounds of formula (VI) may be prepared by substitution of the chloro group in a compound of the formula (VII) with a cyano group. In a typical procedure, a solution of the compound of the formula (VII) in a suitable solvent such as N,N-dimethylformamide is treated with zinc cyanide, tetrakis(triphenylphosphine)-palladium(0) and an acid acceptor such as triethylamine and heated under an atmosphere of nitrogen to between 80 and 120° C., preferably to 100° C. The product of the reaction is usually contaminated with an amount of the corresponding compound of the formula (V) which may be separated by routine chromatography. Compounds of the formula (VII) may be prepared by reaction of a compound of the formula (VIII) with an amine of the formula $R^1NH_2$ (XII).

In a typical procedure, a solution of the compound of the formula (VIII) in a suitable solvent such as isopropyl alcohol is treated with the compound of the formula (XII) and heated at reflux, optionally in the presence of an acid acceptor such as N-ethyl-N-isopropyl-2-propylamine. Compounds of the formula (VIII) may be prepared by protection of 2,6-dichloro-9H-purine (IX). Examples of suitable protecting groups P³ will be apparent to the skilled person [see for instance 'Protecting Groups in Organic Synthesis (Second Edition)', Theodora W. Green and Peter G. M. Wuts, John Wiley and Sons, 1991]. A preferred protecting group is that in which P³ represents tetrahydropyran-2-yl. Suitable conditions for the protection are well known in the art [see for instance 'Protecting Groups in Organic Synthesis (Second Edition)', Theodora W. Green and Peter G. M. Wuts, John Wiley and Sons, 1991]. In a typical procedure, where P³ is tetrahydropyran-2-yl, a solution of 2,6-dichloro-9H-purine (IX) and an acid catalyst such as 4-toluenesulphonic acid monohydrate in a suitable solvent such as ethyl acetate is heated to between 30 and 70° C., preferably to 50° C., and treated with a solution of 2,3-dihydropyran in a suitable solvent such as ethyl acetate.

All the compounds of the formula (I) can also be prepared according to the route shown in Scheme 2, wherein R⁹, P¹, P² and P³ are as defined above.

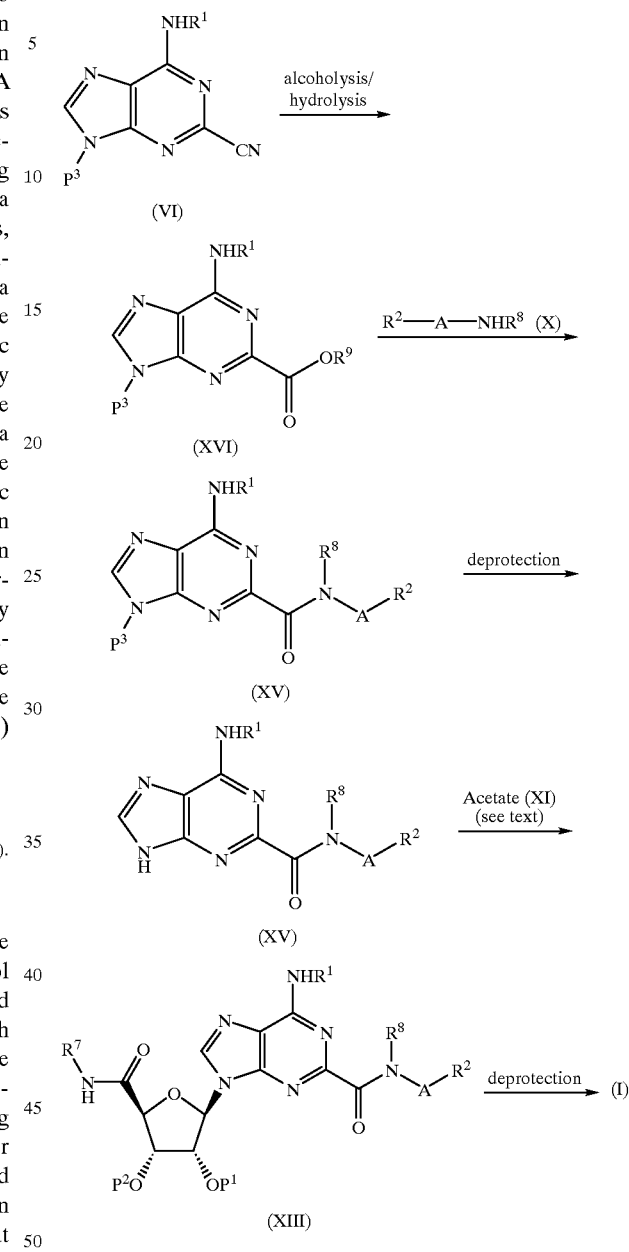

In Scheme 2, the compounds of formula (I) may be prepared by deprotection of a compound of the formula (XIII). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where P¹ and P² are each benzoyl, the protecting groups may be removed by treating a solution of the compound of the formula (XIII) in a suitable solvent, such as methanol, with a base such as potassium carbonate, typically at room temperature. Compounds of the formula (XIII) may be prepared by reaction of a compound of the formula (XI):

(XI)

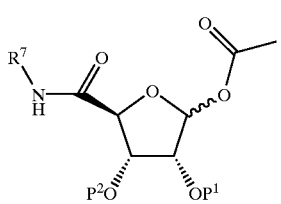

Scheme 3

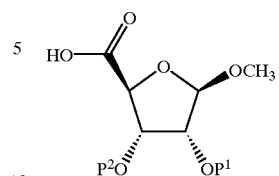

(XVIII)

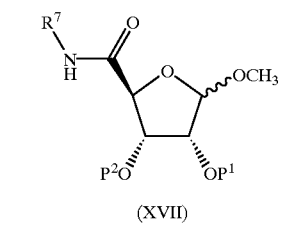

(XVII)

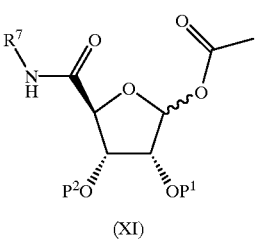

(XI)

(in which $P^1$ and $P^2$ are as defined above) with trimethylsilyl trifluoromethanesulfonate and a compound of the formula (XIV) which has been derivatised with N,O-bis(trimethylsilyl)acetamide. In a typical procedure, the compound of the formula (XIV) is heated in the presence of a suitable solvent, such as 1,1,1-trichloroethane, and N,O-bis(trimethylsilyl)acetamide at an elevated temperature, preferably at reflux. The mixture is then allowed to cool and the solvent is removed. The residue is treated with a solution of the compound of the formula (XI) in a suitable solvent such as toluene followed by trimethylsilyl trifluoromethanesulfonate and the mixture is heated under a nitrogen atmosphere at a temperature between room temperature and the reflux temperature of the chosen solvent to give the compound of the formula (XIII). In the case of toluene, for example, a temperature of 90° C. is preferred. Compounds of the formula (XIV) may be prepared by deprotection of a compound of the formula (XV). Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^3$ is tetrahydropyran-2-yl, the protecting group may be removed by treating a solution of the compound of the formula (XV) in a suitable solvent, such as ethanol, with an acid such as hydrochloric acid. Compounds of the formula (XV) may be prepared by reaction of an ester of the formula (XVI) with an amine of the formula (X):

$$R^2\text{---}A\text{---}NHR^8 \quad (X)$$

at an elevated temperature, preferably at 100 to 150° C. In a typical procedure, the compound of the formula (XVI) and the amine of the formula (X) are heated together at 130° C. Compounds of the formula (XVI) may be prepared by a sequence of alcoholysis and hydrolysis performed on a nitrile of the formula (VI). In a typical procedure, a solution of the nitrile of the formula (VI) in an alcoholic solvent $R^9OH$ is treated with the sodium alkoxide of the formula $R^9ONa$ and heated under reflux. The resulting mixture is cooled, evaporated, dissolved in a suitable solvent such as a mixture of tetrahydrofuran and water (preferably 3:1 by volume) and treated with an acid such as acetic acid. The resulting mixture is heated at an elevated temperature, preferably under reflux, to give the compound of the formula (XVI).

Compounds of the formula (XI), as used in Schemes 1 and 2, may be prepared as shown in Scheme 3, wherein $P^1$ and $P^2$ are as defined above.

Compounds of the formula (XI) may be prepared by treatment of a compound of the formula (XVII) with a mixture of acetic acid, acetic anhydride and a strong acid such as hydrochloric or sulphuric acid with cooling (typically to −10° C.). A compound of formula (XVII) may be prepared from an acid of the formula (XVIII) by activation of the acid as, for example, an acid chloride and treatment of this activated intermediate with an amine of the formula (XIXa):

$$R^7NH_2 \quad (XIXa).$$

In a typical procedure, a compound of formula (XVIII) is dissolved in a suitable inert solvent (e.g. dichloromethane) and treated with oxalyl chloride and a catalytic amount of N,N-dimethylformamide. After removal of excess solvent and reagent by evaporation under reduced pressure, the residue is dissolved in anhydrous dichloromethane and treated with an amine of the formula (XIXa). With regard to the conditions employed in later steps, it may be appropriate to change the protecting groups $P^1$ and $P^2$ in compounds of formula (XVII). Alternative, suitable protecting groups are well-known to the skilled person [e.g. 'Protecting Groups in Organic Synthesis (Second Edition)', Theodora W. Green and Peter G. M. Wuts, John Wiley and Sons, 1991]. In a typical case, a solution of the compound of formula (XVII) wherein $P^1$ and $P^2$ taken together are dimethylmethylene in a suitable solvent such as methanol may treated with an acid such as pyridinium para-toluenesulphonate to give a compound of formula (XVII) wherein $P^1$ and $P^2$ are both replaced by H which may be subsequently reprotected with other functionality. For instance, the compound of formula (XVII) wherein $P^1$ and $P^2$ are both replaced by H may be dissolved in a suitable solvent such as dichloromethane and the resulting solution may be treated with an acid acceptor, such as pyridine, and benzoyl chloride to give a compound of formula (XVII) wherein $P^1$ and $P^2$ are each benzoyl. Compounds of formula (XVIII) are known in the art, for example in *J. Amer. Chem. Soc.,* 1958, 80, 5168 where $P^1$ and $P^2$ taken together are dimethylmethylene.

Amines of the formulae $R^7NH_2$ (XIXa), $R^1NH_2$ (XII) and $R^2$—A—$NHR^8$ (X) are either commercially available or may be prepared by standard techniques well known to persons skilled in the art.

All the compounds of the formula (I) may alternatively be prepared by condensation of an acid of the formula (XIX) with an amine of the formula (X) as shown in Scheme 4.

Scheme 4

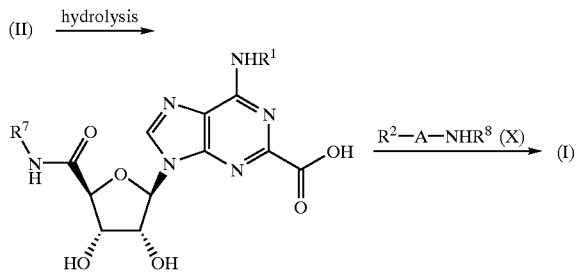

The condensation is typically carried out under conventional peptide-coupling conditions. For example, a solution of the acid (XIX) in a suitable solvent such as dichloromethane may be treated firstly with a suitable coupling agent such as carbonyl diimidazole and subsequently with a compound of the formula (X). An acid of the formula (XIX) may be prepared by hydrolysis of a compound of the formula (II). In order to carry out the hydrolysis, a compound of the formula (II) is typically dissolved in a suitable solvent such as ethanol and treated with a suitable base such as aqueous sodium hydroxide.

Compounds of the formula (I) may alternatively be prepared by an aminocarbonylation reaction of a compound of the formula (XIXb):

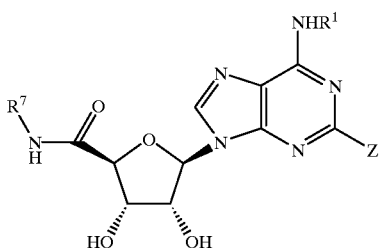

wherein Z is a suitable leaving group such as bromo, iodo, $Sn(C_1-C_{12}\ alkyl)_3$ or $CF_3SO_2O$—, preferably iodo, with a compound of formula $R^2$—A—$NHR^8$ (X) in the presence of carbon monoxide and a suitable coupling catalyst. Preferably, the catalyst is a palladium (II) catalyst, more preferably 1,1'- bis(diphenylphosphino) ferrocenedichloropalladium (II) (optionally as a 1:1 complex with dichloromethane). Alternatively, palladium (II) acetate may be used in the presence of a suitable ligand such as 1,1'- bis(diphenylphosphino)ferrcene, triphenlyphospine, tri(o-tolyl)phosphine or (R)—, (S)— or racemic 2,2'-bis (diphenylphosphino)-1,1'-binaphthyl.

In a typical procedure the reaction is carried out in a sealed vessel in the presence of carbon monoxide at an elevated pressure, e.g. about 345 kPa (50 psi), at an elevated temperature, e.g. about 60° C., and in a suitable solvent, e.g. tetrahydrofuran, methanol or ethanol. Optionally, a suitable organic base may be present such as tertiary amine, e.g. triethylamine, N-ethyldiisopropylamine or 4-methylmorpholine.

The intermediates of the formula (XIXc) can be prepared as shown in Scheme 5.

Scheme 5

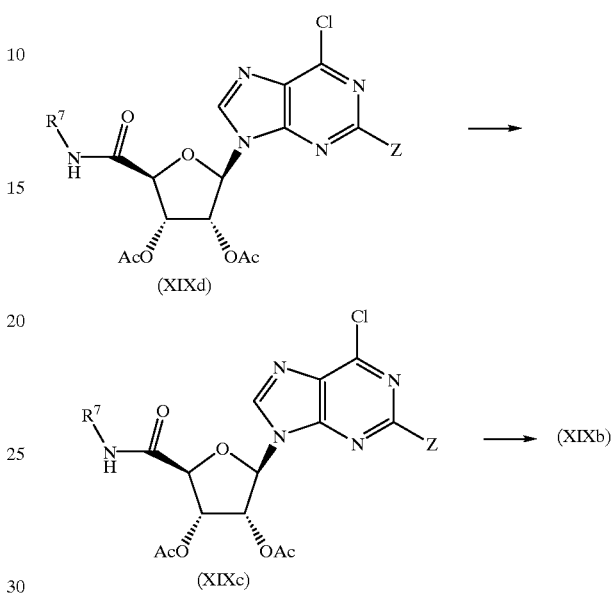

wherein Z is as previously defined for the compound of the formula (XIXb) and Ac is acetyl.

In a typical procedure a compound of the formula (XIXd) is reacted with an amine of the formula $R^1NH_2$ (XII) in the presence of a suitable acid acceptor, e.g. triethylamine, and in a suitable solvent, e.g. acetonitrile, at an elevated temperature, if necessary. The product of the formula (XIXc) obtained can be deprotected by hydrolysis to provide a compound of the formula (XIXb) by a conventional procedure such as by using a suitable inorganic base, e.g. sodium carbonate, sodium hydroxide, potassium hydroxide, lithium hydroxide, sodium carbonate, potassium carbonate or caesium carbonate, and in a suitable solvent, e.g. methanol, ethanol, isopropanol, 1,2-dimethoxyethane, tetrahydrofuran, dimethylformamide, acetone, 2-butanone or 4-methyl-2-pentanone, optionally under aqueous conditions, at from 0° C. to the reflux temperature of the solvent, e.g. room temperature. Alternatively, the deprotection can be carried out using a suitable amine base such as triethylamine, diisopropylethylamine, 4-methylmorpholine, ammonia, methylamine, ethylamine or dimethylamine in a suitable solvent such as methanol, ethanol, n-propanol, isopropanol, tetrahydrofuran or dicholromethane at from 0° C. to the reflux temperature of the solvent. Compounds of the formula (XIXd) can be prepared by a conventional procedure.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This is evaluated by determining the compound profile in an assay where superoxide production was measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

In this assay, the compounds of the invention have $IC_{50}$ values of less than 200 n M. The compounds of Examples 7, 10, 12, 16, 20, 21, 27 and 31 are most effective and have $IC_{50}$ values of less than 40 n M.

The present invention thus also provides a pharmaceutical composition including a compound of the formula (I) as defined above, or a pharmaceutically acceptable salt or solvate thereof, together with a pharmaceutically acceptable excipient, diluent or carrier.

The present invention also provides a compound of the formula (I) as defined above, or a pharmaceutically acceptable salt, solvate or composition thereof, for use as a medicament.

The present invention also provides a compound of the formula (I) as defined above, or a pharmaceutically acceptable salt, solvate or composition thereof, for use as a medicament to treat a disease for which a A2a receptor agonist is indicated.

The present invention also provides the use of a compound of the formula (I) as defined above, or of a pharmaceutically acceptable salt, solvate or composition thereof, for the manufacture of a medicament to treat a disease for which a A2a receptor agonist is indicated.

The present invention also provides a compound of the formula (I) as defined above, or a pharmaceutically acceptable salt, solvate or composition thereof, for use as an anti-inflammatory agent.

The present invention also provides the use of a compound of the formula (I) as defined above, or of a pharmaceutically acceptable salt, solvate or composition thereof, for the manufacture of an anti-inflammatory agent.

The present invention also provides the use of a compound of the formula (I) as defined above, or of a pharmaceutically acceptable salt, solvate or composition thereof, for the manufacture of a medicament for the treatment of a respiratory disease. The present invention also provides the use as referred to above where the disease is selected from the group consisting of adult respiratory distress syndrome (ARDS), bronchitis, chronic bronchitis, chronic obstructive pulmonary disease, cystic fibrosis, asthma, emphysema bronchiectasis, chronic sinusitis and rhinitis.

The present invention also provides the use of a compound of the formula (I) as defined above, or of a pharmaceutically acceptable salt, solvate or composition thereof, for the manufacture of a medicament for the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, Heliobacter pylori-gastritis, non-Heliobacter pylori gastritis, non-steroidal anti-inflammatory drug-induced damage to the gastro-intestinal tract or a psychotic disorder, or for wound healing.

The present invention also provides a method of treatment of a mammal, including a human being, to treat a disease for which a A2a receptor agonist is indicated including treating said mammal with an effective amount of a compound of the formula (I) as defined above or with a pharmaceutically acceptable salt, solvate or composition thereof.

The present invention also provides a method of treatment of a mammal, including a human being, to treat an inflammatory disease including treating said mammal with an effective amount of a compound of the formula (I) as defined above or with a pharmaceutically acceptable salt, solvate or composition thereof.

The present invention also provides a method of treatment of a mammal, including a human being, to treat a respiratory disease including treating said mammal with an effective amount of a compound of the formula (I) as defined above or with a pharmaceutically acceptable salt, solvate or composition thereof. The present invention also provides the method as referred to above, wherein the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

The present invention also provides a method of treatment of a mammal, including a human being, to treat septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, Heliobacter pylori-gastritis, non-Heliobacter pylori gastritis, non-steroidal anti-inflammatory drug-induced damage to the gastro-intestinal tract or a psychotic disorder, or for wound healing, including treating said mammal with an effective amount of a compound of the formula (I) as defined above or with a pharmaceutically acceptable salt, solvate or composition thereof.

The compounds of the formula (I) can be administered alone but will generally be administered in admixture with a suitable pharmaceutically acceptable excipient, diluent or carrier selected with regard to the intended route of administration and standard pharmaceutical practice.

For example, the compounds of the formula (I) can be administered orally, buccally or sublingually in the form of tablets, capsules, ovules, elixirs, solutions or suspensions, which may contain flavouring or colouring agents, for immediate-, delayed-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or a high molecular weight polyethylene glycol. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol or glycerin, and combinations thereof.

The compounds of the formula (I) can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.01 to 100 mg/kg, body weight of the subject to be treated, preferably from 0.1 to 100 mg/kg (in single or divided doses).

Thus tablets or capsules of the compound of the formula (I) may contain from 5 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 to 4000 μg of a compound of the formula (I) for delivery to the patient. The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment, gel, suspension, dusting powder, spray or drug-incorporated dressing (e.g. a tulle dressing, a white soft paraffin or polyethylene glycol impregnated gauze dressing, or hydrogel, hydrocolloid, alginate or film dressing). The compounds of the formula (I) may also be transdermally administered, for example, by the use of a skin patch.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. They can also be formulated as a hydrogel with cellulose or polyacrylate derivatives or other viscosity modifiers.

It is to be appreciated that all references herein to treatment include curative, palliative and prophylactic treatment.

EXAMPLES

The following Examples illustrate the preparation of the compounds of the formula (I). $^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded in the thermospray ionisation mode. The following abbreviations have been used for common solvents: $CDCl_3$, deuterochloroform; DMSO, dimethylsulphoxide; THF, tetrahydrofuran. Where thin layer chromatography (TLC) has been used it refers to silica gel TLC using silica gel 60 $F_{254}$ plates, $R_f$ is the distance travelled by a compound divided by the distance travelled by the solvent front on a TLC plate.

Example 1

6-[(2,2-Diphenylethyl)amino]-9-{(2R,3R,4S,5S)-5-[(ethylamino)carbonyl]-3,4-dihydroxytetrahydro-2-furanyl}-N-[2-(1-piperidinyl)ethyl]-9H-purine-2-carboxamide

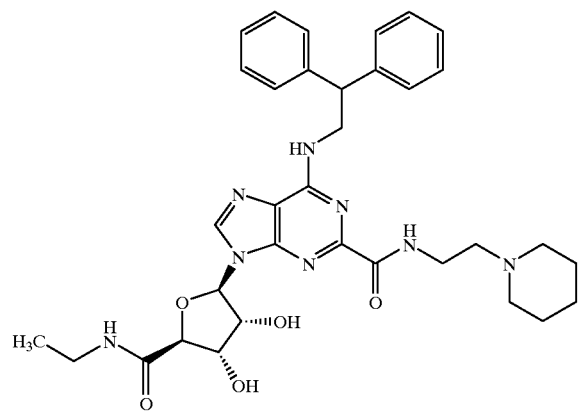

A solution of (2R,3R,4R,5S)-4-(benzoyloxy)-2-[6-[(2,2-diphenylethyl)amino]-2-({[2-(1-piperidinyl)-ethyl]amino}carbonyl)-9H-purin-9-yl]-5-[(ethylamino)carbonyl] tetrahydro-3-furanyl benzoate (Preparation 7) (104 mg, 0.12 mmol) in methanol (3 ml) was treated with potassium carbonate (100 mg, 0.72 mmol). The mixture was stirred at room temperature for 30 minutes. The solvent was removed under reduced pressure and the residue was partitioned between ethyl acetate and water. The organic layer was separated, dried with anhydrous magnesium sulphate, filtered and evaporated under reduced pressure. The residue was purified by column chromatography on silica gel eluting with dichloromethane: methanol (90:10 by volume) to afford the title compound as a white solid (44 mg).

$^1$H—NMR (400 MHz, CDCl$_3$) δ: 8.76 (1H, s), 8.67 (1H, br m), 7.63 (1H, br m), 7.38–7.19 (10H, m), 6.92 (1H, m), 6.07 (1H, br m), 5.10 (2H, m), 4.55 (1H, m), 4.36 (4H, m), 3.52 (2H, m), 3.40 (2H, m), 2.60 (2H, br m), 2.40 (4H, br m), 1.37 (6H, m), 1.23 (3H, t). LRMS (thermospray): m/z [MH$^+$] 643, [Mna$^+$] 665.

Example 2

6-[(2,2-Diphenylethyl)amino]-9-{(2R,3R,4S,5S)-5-[(ethylamino)carbonyl]-3,4-dihydroxytetrahydro-2-furanyl}-N-[2-(4-isopropyl-1-piperidinyl)ethyl]-9H-purine-2-carboxamide

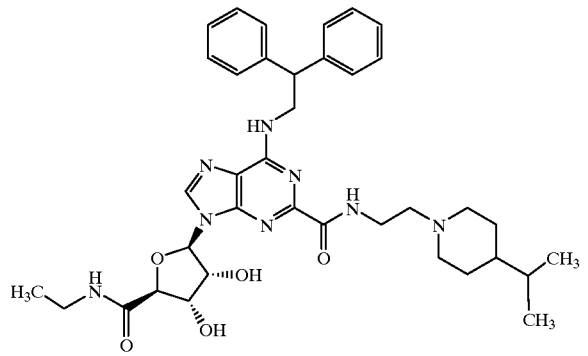

Methyl 6-[(2,2-diphenylethyl)amino]-9-{(2R,3R,4S,5S)-5-[(ethylamino) carbonyl]-3,4-dihydroxytetra-hydro-2-furanyl}-9H-purine-2-carboxylate (Preparation 11) (100 mg, 0.18 mmol) and 2-(4-isopropyl-1-piperidinyl)ethylamine (Preparation 17) (300 mg, 1.76 mmol) were heated at 120° C. under a nitrogen atmosphere for three hours. The reaction mixture was allowed to cool to room temperature and purified by column chromatography on silica gel eluting with dichloromethane:methanol:concentrated aqueous ammonia (90:10:1 by volume) to afford the title compound as a white solid (76 mg, 62%).

$^1$H—NMR (400 MHz, CDCl$_3$) δ: 8.80 (1H, br s), 8.60 (1H, br s), 7.55 (2H, br m), 7.35–7.20 (10H, m), 6.95 (1H, br m), 5.95 (1H, br m), 5.10 (2H, m), 4.50 (1H, br m), 4.40–4.20 (5H, m), 3.60–3.30 (5H, m), 2.85 (1H, br m), 2.60 (2H, br m), 1.95 (1H, br m), 1.60–1.50 (3H, br m), 1.30–0.90 (6H, m), 0.80 (6H, d).

LRMS (thermospray): m/z [MH$^+$] 686.

Examples 3–34

Examples 3 to 33 were prepared by a similar method to that used for Example 2 or Example 34 (for Examples 10, 11, 20, and 28). Mass spectroscopy data was obtained by the electrospray method.

Example 3

6-[(2,2-diphenylethyl)amino]-9-{(2R,3R,4S,5S)-5-[(ethylamino)carbonyl]-3,4-dihydroxytetrahydro-2-furanyl}-N-(2-pyridinylmethyl)-9H-purine-2-carboxamide

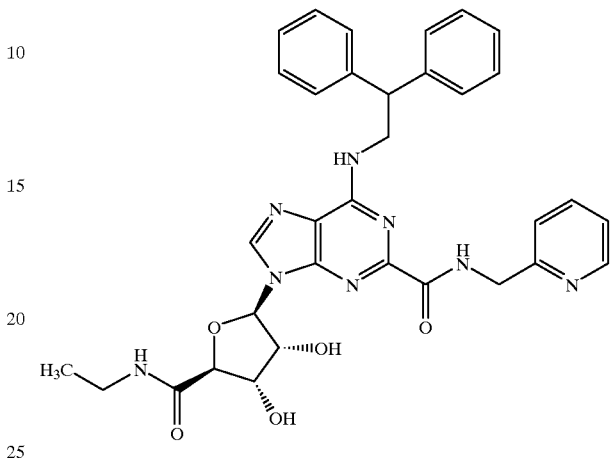

H—NMR (400 MHz, CDCl$_3$)δ: 9.35 (1H, br s), 8.75 (1H, s), 8.30 (1H, br s), 7.70 (1H, t), 7.40 (1H, br s), 7.35–7.15 (10H, m), 6.85 (1H, m), 6.60 (1H, m), 5.00 (1H, s), 4.75 (2H, m), 4.55 4.30 (5H, m), 3.40 (2H, m), 1.20 (3H, t).

[MH$^+$] 623, [MNa$^+$] 645

Example 4

N-benzyl-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

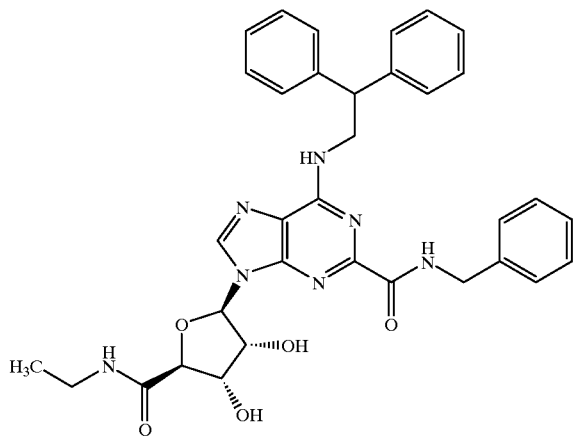

H—NMR (400 MHz, CDCl$_3$)δ: 8.85 (1H, s), 8.50 (1H, br s), 7.40–7.10 ] (15H, m), 6.95 (1H, d), 6.80 (1H, br s), 5.10 (1H, s), 4.65 (2H, m), 4.50 (1H, m), 4.35 (2H, m), 4.25 (2H, m), 3.25 (2H, m), 1.05 (3H, t).

[MH] 622, [MNa$^+$] 644

Example 5

6-[(2,2-diphenylethyl)amino]-9-{(2R,3R,4S,5S)-5-[(ethylamino)carbonyl]-3,4-dihydroxytetrahydro-2-furanyl}-N-(2-phenylethyl)-9H-purine-2-carboxamide

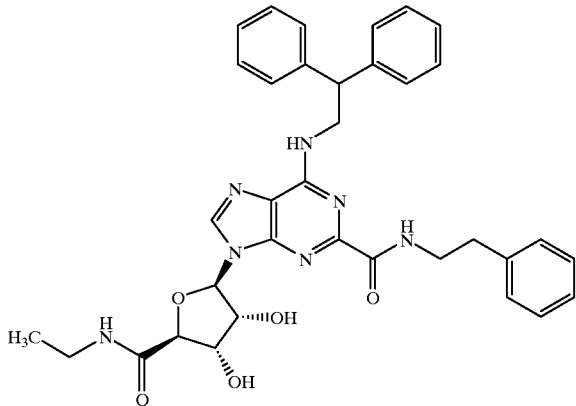

H—NMR (400 MHz, CDCl₃)δ:

δ:8.80 (1H, s), 8.20 (1H, m), 7.45 (1H, m), 7.40–7.10 (15H, m), 6.95 (1H, d), 6.30 (1H, br s), 5.10 (1H, s), 4.50 (1H, m), 4.35 (2H, m), 4.20 (1H, br s), 3.70 (2H, m), 3.40 (2H, m), 2.90 (2H, t), 1.20 (3H, t).

[MH⁺] 636, [MNa⁺] 658

Example 6

N-[2-(dimethylamino)ethyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

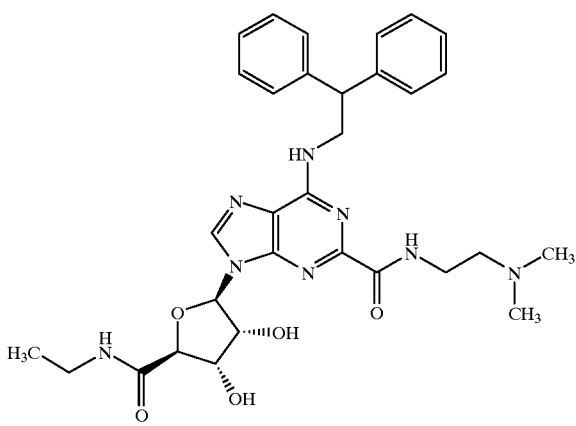

H—NMR (400 MHz, CDCl₃)δ:

δ:8.80 (2H, s), 7.70–7.45 (2H, m), 7.35–7.20 (10H, m), 6.95 (1H, d), 6.00 (1H, br s), 5.20 (1H, m), 5.10 (1H, m), 4.50 (1H, s), 4.40–4.20 (4H, m), 3.55–3.35 (4H, m), 2.55 (2H, m), 2.10 (6H, s), 1.20 (3H, t).

[MH⁺] 604

Example 7

6-[(2,2-diphenylethyl)amino]-9-{(2R,3R,4S,5S)-5-[(ethylamino)carbonyl]-3,4-dihydroxytetrahydro-2-furanyl}-N-[3-(1-pyrrolidinyl)propyl]-9H-purine-2-carboxamide

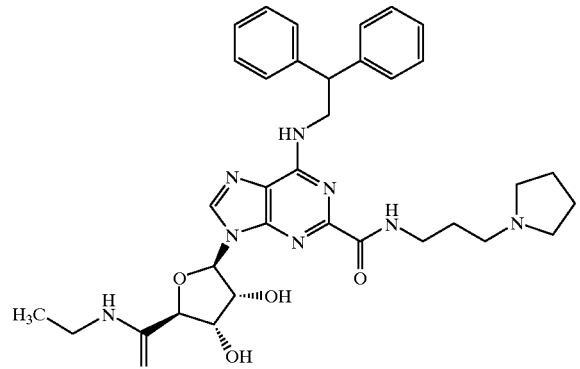

H—NMR (400 MHz, CDCl₃)δ:

δ: 8.75 (1H, br s), 8.40 (1H br s), 7.35–7.20 (10H, m), 6.90 (1H, br s), 6.00 (1H, br s), 5.10 (2H, m), 4.60 (1H, br s), 4.40–4.20 (4H, m), 3.55 (2H, m), 3.40 (2H, m), 2.60–2.40 (6H, m), 1.85 (2H, m), 1.70 (4H, br s), 1.20 (3H, t).

[MH⁺] 644

Example 8

6-[(2,2-diphenylethyl)amino]-9-{(2R,3R,4S,5S)-5-[(ethylamino)carbonyl]-3,4-dihydroxytetrahydro-2-furanyl}-N-[2-(2-pyridinyl)ethyl]-9H-purine-2-carboxamide

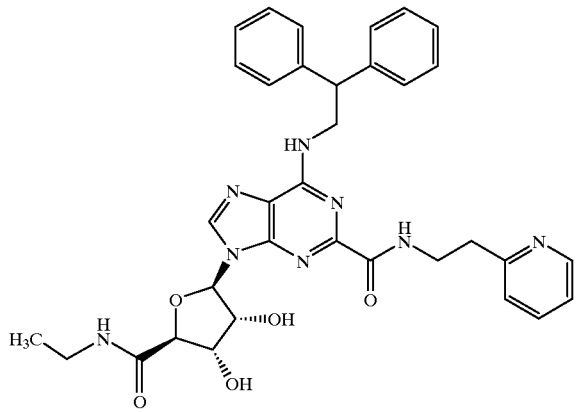

H—NMR (400 MHz, CDCl₃)δ:

δ:9.02 (1H, m), 8.80 (1H, s), 8.06 (1H, br s), 7.77 (1H, s), 7.61 (1H, m), 7.50 (1H, t), 7.23–7.39 (10H, m), 7.12 (1H, d), 7.00 (1H, d), 6.92 (1H, m), 5.95 (1H, br s), 5.18 (1H, d), 5.11 (1H, s), 4.55 (1H, d), 4.18–4.42 (4H, m), 3.88 (2H, m), 3.43 (2H, m), 3.11 (2H, t), 1.22 (3H, t)

[MH⁺] 638, [MNa⁺] 660

Example 9

6-[(2,2-diphenylethyl)amino]-9-{(2R,3R,4S,5S)-5-[(ethylamino)carbonyl]-3,4-dihydroxytetrahydro-2-furanyl}-N-[2-(4-morpholinyl)ethyl]-9H-purine-2-carboxamide

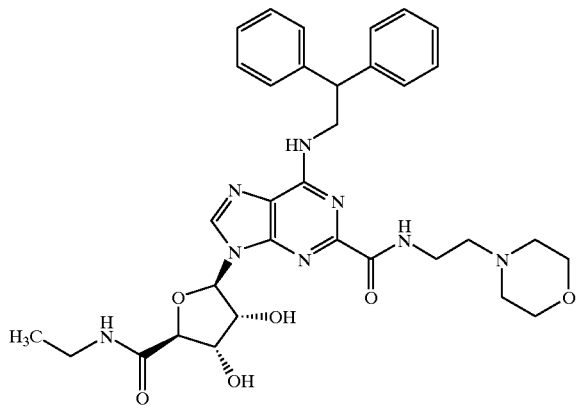

H—NMR (400 MHz, CDCl₃)δ:

δ8.80 (1H, s), 8.65 (1H, br s), 7.60 (1H, br s), 7.50 (1H, br s), 7.20–7.40 (10H, m), 6.95 (1H, d), 6.00 (1H, br d), 5.10 (2H, m), 4.55 (1H, d), 4.20–4.40 (4H, m), 3.30–3.60 (8H, m), 2.60 (2H, t), 2.40 (4H, m),1.25 (3H, t)

[MH⁺] 646, [MNa⁺] 668

Example 10

9-{(2R,3R,4S, 5S)-5-[(ethylamino)carbonyl]-3,4-dihydroxytetrahydro-2-furanyl}-6-[(1-ethylpropyl)amino]-N-[2-(1-piperidinyl)ethyl]-9H-purine-2-carboxamide

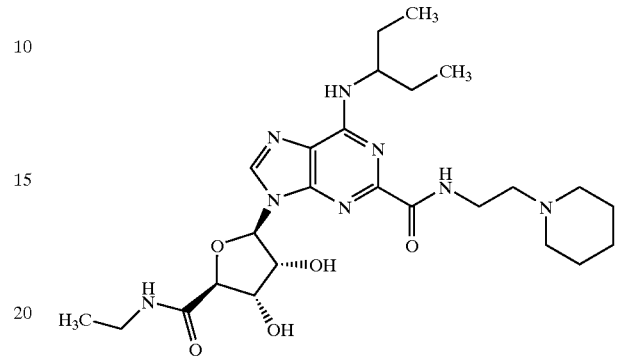

H—NMR (400 MHz, CD₃OD)δ:

δ: 8.45 (1H, s), 6.10 (1H, d), 4.85 (1H, t), 4.35–4.50 (3H, m), 3.60 (2H, t), 3.25–3.45 (3H, m), 2.40–2.70 (6H, m), 1.40–1.80 (10H, m), 1.05 (3H, t), 0.95 (6H, m)

[MH⁺] 534, [MNa⁺] 556

Example 11

6-{[(1S)-1-benzyl-2-hydroxyethyl]amino}-9-{(2R, 3R,4S,5S)-5-[(ethylamino)carbonyl]-3,4-dihydroxytetrahydro-2-furanyl}-N-[2-(1-piperidinyl)ethyl]-9H-purine-2-carboxamide

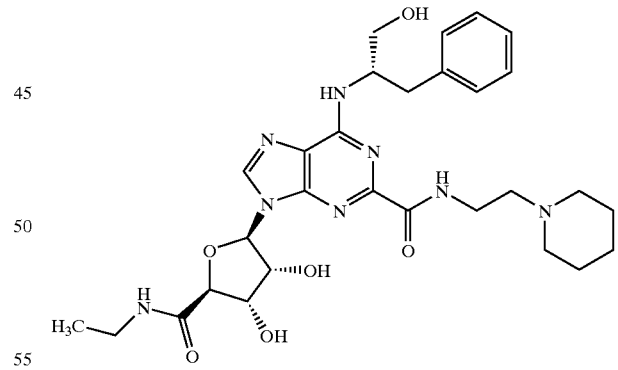

H—NMR (400 MHz, CD₃OD)δ

δ: 8.45 (1H, s), 7.30 (2H, m), 7.15 (2H, m), 7.05 (1H, m), 6.10 (1H, d), 4.80 (1H, t), 4.45 (1H, s), 4.40 (1H, d), 3.70 (2H, m), 3.55 (2H, m), 3.20–3.45 (2H, m), 3.10 (1H, m), 2.95 (1H, m), 2.40–2.70 (7H, m), 1.65 (4H, m), 1.50 (2H, m), 1.05 (3H, t)

[MH⁺] 598, [MNa⁺] 620

Example 12

6-[(2,2-diphenylethyl)amino]-9-{(2R,3R,4S,5S)-5-[(ethylamino)carbonyl]-3,4-dihydroxytetrahydro-2-furanyl}-N-[2-(4-isopropyl-1-piperidinyl)ethyl]-9H-purine-2-carboxamide

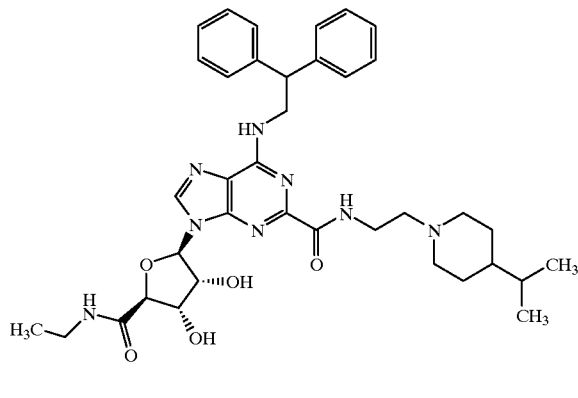

H—NMR (400 MHz, CDCl₃)δ:

δ: 8.80 (1H, br s), 8.55 (1H, br s), 7.65 (2H, br m), 7.55 (1H, br s), 7.20–7.35 (10H, m), 6.95 (1H, br d), 5.95 (1H, br s), 5.05–5.15 (2H, m), 4.55 (1H, br s), 4.20–4.45 (4H, m) 3.30–3.60 (4H, m), 2.85 (2H, br s), 2.55 (2H, br s), 1.95 (2H, br t), 0.90–1.55 (9H, m) 0.80 (6H, d)

[MH⁺] 686, [MNa⁺] 708

Example 13

N-[2-(3,4-dihydro-2(1H)-isoquinolinyl)ethyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

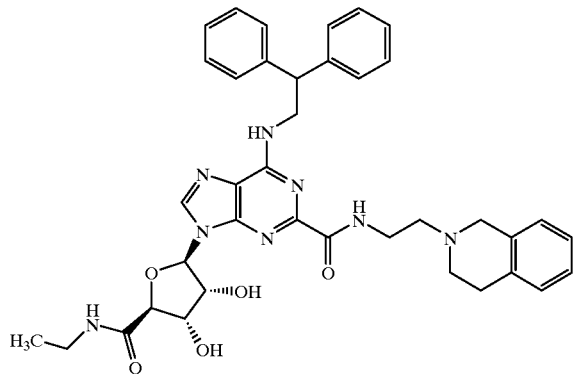

H—NMR (400 MHz, CDCl₃)δ:

δ: 8.75 (1H, br s), 8.60 (1H, br s), 7.50 (2H, br m), 6.85–7.30 (15H, m), 5.85 (1H, br s), 5.05 (2H, br m), 4.50 (1H, br s), 4.05–4.40 (4H, m), 3.50–3.75 (4H, m), 3.40 (2H, m), 2.60–2.90 (6H, m), 1.20 (3H, t)

[MH⁺] 692, [Mna⁺] 714

Example 14

6-[(2,2-diphenylethyl)amino]-9-{(2R,3R,4 S,5S)-5-[(ethylamino)carbonyl]-3,4-dihydroxytetrahydro-2-furanyl}-N-(4-piperidinylmethyl)-9H-purine-2-carboxamide

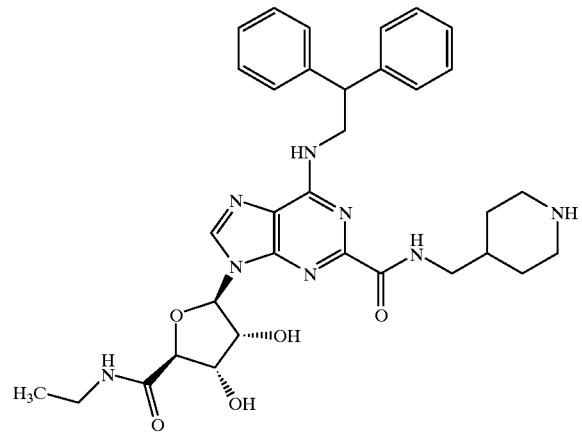

H—NMR (400 MHz, CDCl₃+DMSO-d6)

δ: 8.45 (1H, s), 8.10 (1H br s), 7.00–7.40 (11H, m), 6.55 (1H, br s), 6.25 (1H, br s), 4.15–4.90 (6H, m), 3.15–3.50 (4H, m), 3.00–3.15 (2H, m), 1.55–1.75 (3H, m), 0.90–1.40 (5H, m)

[MH⁺] 630, [MNa⁺] 652

Example 15

6-[(2,2-diphenylethyl)amino]-9-{(2R,3R,4S,5S)-5-[(ethylamino)carbonyl]-3,4-dihydroxytetrahydro-2-furanyl}-N-[4-(1-piperidinyl)butyl]-9H-purine-2-carboxamide

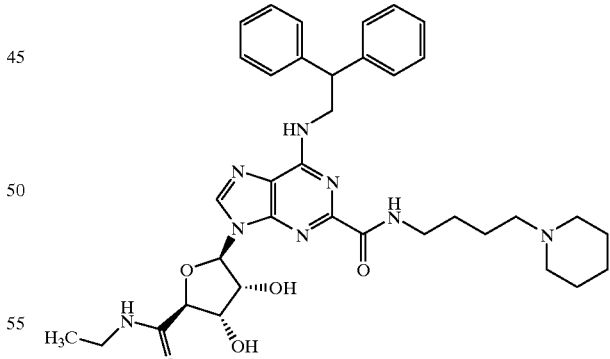

H—NMR (400 MHz, CDCl₃)δ:

δ: 8.73 (1H, m), 8.56–8.42 (1H, m), 7.52–7.40 (1H, m), 7.40–7.26 (10H, m), 6.90 (1H, m), 6.06–5.94 (1H, m), 5.05 (1H, m), 4.69–4.53 (1H, m), 4.45–4.16 (4H, m), 3.61–3.29 (4H, m), 2.77–2.60 (3H, m), 1.85–1.73 (2H, m), 1.24–1.14 (3H, m), 1.00–0.93 (6H, m)

[MH⁺] 671

Example 16

6-[(2,2-diphenylethyl)amino]-9-{(2R,3R,4S,5S)-5-[(ethylamino)carbonyl]-3,4-dihydroxytetrahydro-2-furanyl}-N-[3-(isopropylamino)propyl]-9H-purine-2-carboxamide

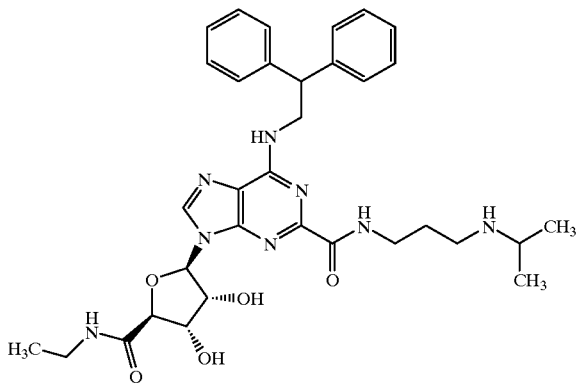

H—NMR (400 MHz, CDCl$_3$)δ:

δ: 8.73 (1H, m), 8.56–8.42 (1H, m), 7.52–7.40 (1H, m), 7.40–7.26 (10H, m), 6.90 (1H, m), 6.06–5.94 (1H, m), 5.05 (1H, m), 4.69–4.53 (1H, m), 4.45–4.16 (4H, m), 3.61–3.29 (4H, m), 2.77–2.60 (3H, m), 1.85–1.73 (2H, m), 1.24–1.14 (3H, m), 1.00–0.93 (6H, m)

[MH$^+$] 631, [MNa$^+$] 653

Example 17

6-[(2,2-diphenylethyl)amino]-9-{(2R,3R,4S,5S)-5-[(ethylamino)carbonyl]-3,4-dihydroxytetrahydro-2-furanyl}-N-[3-(2-pyridinylamino)propyl]-9H-purine-2-carboxamide

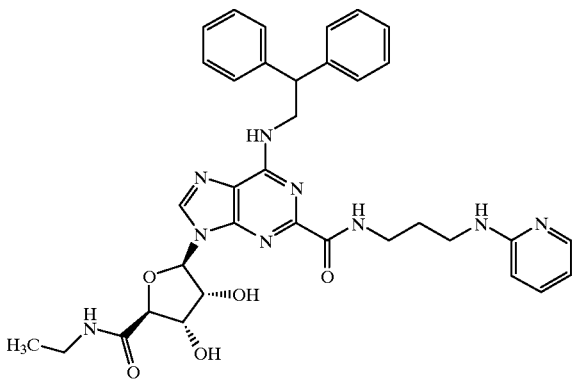

H—NMR (400 MHz, CDl$_3$)δ:

δ: 8.45 (2H, m), 7.80–7.60 (1H, m), 7.40 (1H, m), 7.30–7.00 (10H, m), 6.80–6.64 (1H, m), 6.48 (1H, m), 6.35 (1H, m), 5.03–4.90 (1H, m), 4.77–4.60 (1H, m), 4.52–4.13 (4H, m), 3.68–3.20 (8H, m), 1.97–1.85 (2H, m), 1.20–1.05 (3H, m)

[MH$^+$] 666, [MNa$^+$] 688

Example 18

6-[(2,2-diphenylethyl)amino]-9-{(2R,3R,4S, 5S)-5-[(ethylamino)carbonyl]-3,4-dihydroxytetrahydro-2-furanyl}-N-{3-[methyl(phenylsulfonyl)amino]propyl}-9H-purine-2-carboxamide

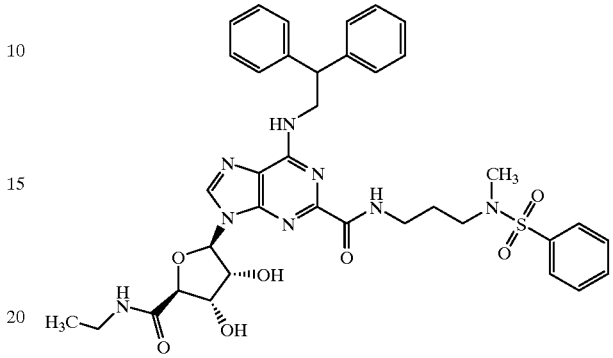

H—NMR (400 MHz, CDCl$_3$)δ:

δ: 8.95 (1H, m), 8.76 (1H, m), 7.75 (2H, m), 7.63–7.40 (5H, m), 7.40–7.06 (10H, m), 6.97 (1H, m), 6.00–5.87 (1H, m), 5.16 (1H, m), 5.10 (1H, m), 4.60–4.24 (5H, m), 3.70–3.55 (2H, m), 3.48–3.34 (2H, m), 3.22–3.00 (2H, m), 2.82–2.60 (3H, m), 1.93–1.73 (2H, m), 1.23 (3H, t)

[MH$^+$] 743, [MNa$^+$] 765

Example 19

6-[(2,2-diphenylethyl)amino]-9-{(2R,3R,4S,5S)-5-[(ethylamino)carbonyl]-3,4-dihydroxytetrahydro-2-furanyl}-N-{3-[methyl(methylsulfonyl)amino]propyl}-9H-purine-2-carboxamide

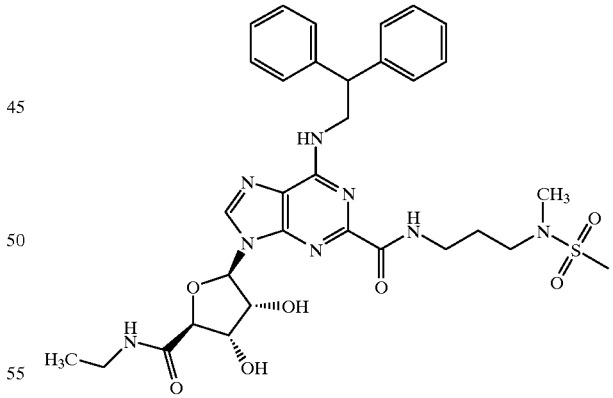

H—NMR (400 MHz, CDCl$_3$)δ:

δ: 8.93–8.80 (1H, m), 8.77–8.68 (1H, m), 7.53–7.45 (1H, m), 7.30–7.20 (10H, m), 6.90 (1H, m), 5.97–5.87 (1H, m), 5.19–5.10 (1H, m), 5.06 (1H, m), 4.56–4.27 (5H, m), 3.64–3.48 (2H, m), 3.47–3.30 (2H, m), 3.30–3.16 (2H, m), 2.90–2.77 (3H, m), 2.60–2.43 (3H, m), 1.90–1.74 (2H, m), 1.22 (3H, t)

[MH$^+$] 681

Example 20

9-{(2R,3R,4S,5S)-5-[(ethylamino)carbonyl]-3,4-dihydroxytetrahydro-2-furanyl}-6-[(9H-fluoren-9-ylmethyl)amino]-N-[2-(1-piperidinyl)ethyl]-9H-purine-2-carboxamide

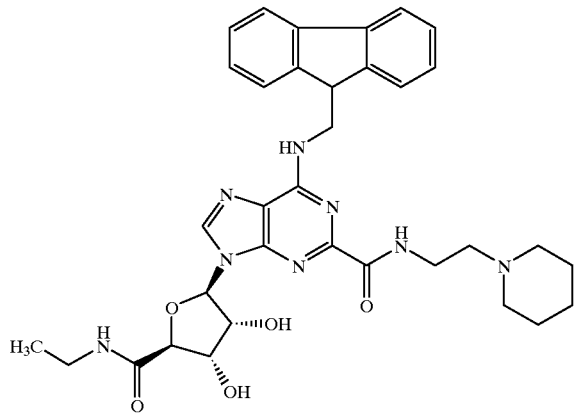

H—NMR (400 MHz, CD$_3$OD)

δ: 8.45 (1H, s), 7.80 (2H, m), 7.68 (2H, m), 7.34 (2H, m), 7.24 (2H, m), 6.13 (1H, m), 4.84 (1H, m), 4.43 (1H, m), 4.40 (2H, m), 4.27–4.18 (2H, m), 3.53 (2H, m), 3.40–3.23 (2H, m), 2.55 (2H, m), 2.50–2.35 (4H, m), 1.55–1.42 (4H, m), 1.42–1.32 (2H, m), 1.06 (3H, t)

[MH$^+$] 641

Example 21

N-[3-(diethylamino)propyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

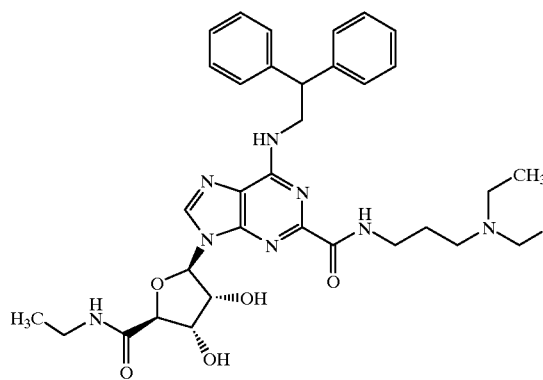

H—NMR (400 MHz, CDCl$_3$)δ:

δ: 8.95–8.60 (2H, m), 7.90–7.65 (1H, m), 7.65–7.50 (1H, m), 7.45–7.30 (10H, m), 7.05–6.90 (1H, m), 6.10–5.85 (1H, m), 5.25–5.05 (2H, m), 4.60–4.50 (1H, m), 4.50–4.20 (4H, m), 3.65–3.30 (4H, m), 2.60–2.50 (2H, m), 2.50–2.30 (4H, m), 1.80–1.70 (2H, m), 1.30–1.15 (3H, m), 1.00–0.85 (1H, m),

[MH$^+$] 645, [MNa$^+$] 667

Example 22

6-[(2,2-diphenylethyl)amino]-9-{(2R,3R,4S,S5S)-5-[(ethylamino)carbonyl]-3,4-dihydroxytetrahydro-2-furanyl}-N-[3-(4-morpholinyl)propyl]-9H-purine-2-carboxamide

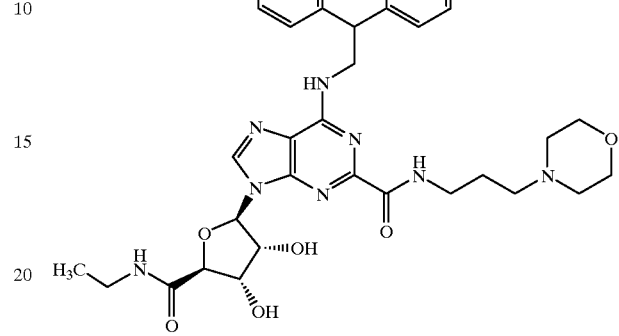

H—NMR (400 MHz CDCl$_3$+DMSO-d6)

δ: 8.65–8.50 (1H, m), 8.30–8.10 (1H, m), 7.60–7.45 (1H, m), 7.35–7.15 (10H, m), 7.15–7.00 (1H, m), 6.75–6.65 (1H, m), 6.30–6.15 (1H, m), 5.00–4.85 (2H, m), 4.50–4.45 (1H, m), 4.45–4.35 (2H, m), 4.35–4.15 (2H, m), 3.65–3.55 (4H, m), 3.55–3.30 (4H, m), 2.45–2.25 (6H, m), 1.85–1.70 (2H, m), 1.15 (3H, t)

[MH$^+$] 659

Example 23

6-[(2,2-diphenylethyl)amino]-9-{(2R,3R,4S,5S)-5-[(ethylamino)carbonyl]-3,4-dihydroxytetrahydro-2-furanyl}-N-[3-(methylamino)propyl]-9H-purine-2-carboxamide

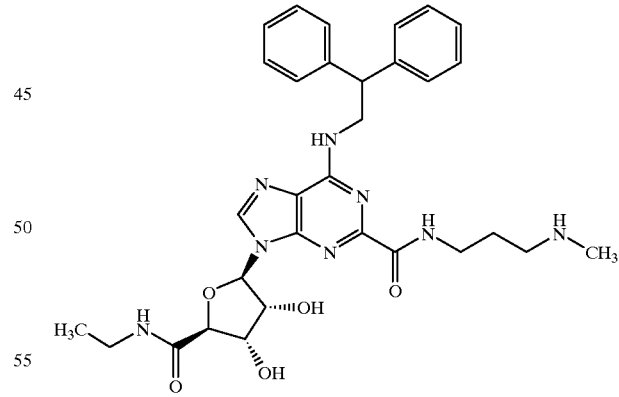

H—NMR (400 MHz, CDCl$_3$)δ:

δ: 9.10–8.95 (1H, m), 8.80–8.70 (1H, m), 7.60–7.50 (1H, m), 7.40–7.25 (10H, m), 7.00–6.85 (1H, m), 6.10–5.90 (1H, m), 5.10–5.05 (1H, m), 4.65–4.55 (1H, m), 4.40–4.20 (4H, m), 3.60–3.45 (2H, m), 3.45–3.30 (2H, m), 2.70–2.60 (2H, m), 2.25–2.15 (3H, m), 1.80–1.70 (2H, m), 1.25–1.10 (3H, m),

[MH$^+$] 603

Example 24

6-[(2,2-diphenylethyl)amino]-9-{(2R,3R,4S,5S)-5-[(ethylamino)carbonyl]-3,4-dihydroxytetrahydro-2-furanyl}-N-[2-(5-methyl-1H-imidazol-4-yl)ethyl]-9H-purine-2-carboxamide

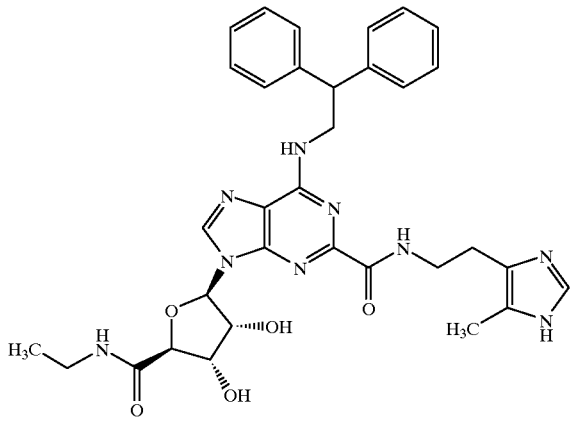

H—NMR (400 MHz, CD₃OD)

δ: 8.20 (1H, s), 7.40–7.10 (11H, m), 6.10 (1H, d), 4.90–4.70 (1H, m), 4.55–4.25 (5H, m), 3.70–3.55 (2H, m), 3.45–3.20 (2H, m), 2.90–2.80 (2H, m), 2.25–2.05 (3H, m), 1.10 (1H, t)

[MH⁺] 640

Example 25

N-[4-(dimethylamino)butyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

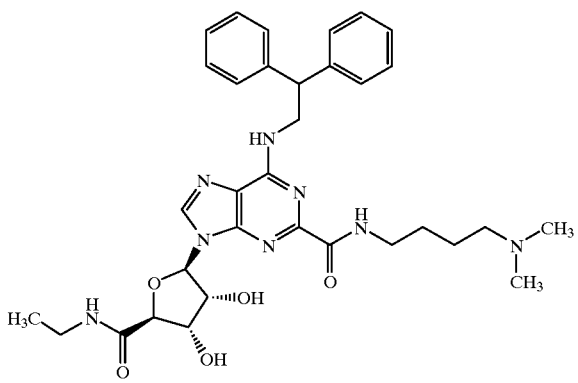

H—NMR (400 MHz, CDCl₃)δ:

δ: 8.60–4.50 (1H, m), 8.20–8.10 (1H, m), 7.35–7.25 (10H, m), 6.80–6.60 (1H, m), 6.10–5.90 (1H, m), 4.45–4.20 (4H, m), 3.70–3.50 (1H, m), 3.45–3.20 (3H, m), 2.60–2.35 (1H, m), 2.30–2.10 (9H, m), 1.80–1.50 (6H, m), 1.15–1.00 (3H, m)

[MH⁺] 631, [MNa⁺] 653

Example 26

6-[(2,2-diphenylethyl)amino]-9-{(2R,3R,4S,5S)-5-[(ethylamino)carbonyl]-3,4-dihydroxytetrahydro-2-furanyl}-N-[3-(4-methyl-1-piperazinyl)propyl]-9H-purine-2-carboxamide

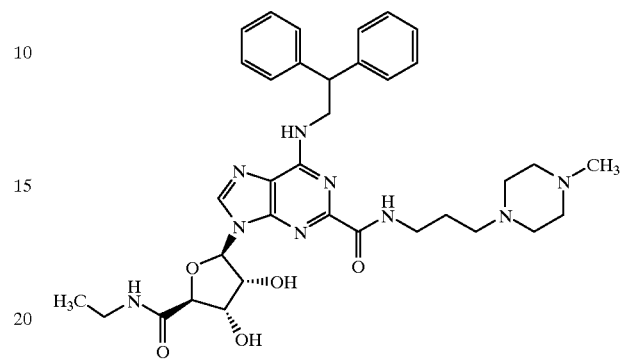

H—NMR (400 MHz, CDCl₃)δ:

δ: 8.90–8.70 (1H, m), 8.35–8.20 (1H, m), 7.70–7.40 (2H, m), 7.40–7.25 (10H, m), 7.00–6.85 (1H, m), 6.10–5.90 (1H, m), 5.20–5.00 (2H, m), 4.65–4.50 (1H, m), 4.45–4.20 (4H, m), 3.60–3.30 (4H, m), 2.55–2.30 (8H, m), 2.30–2.15 (3H, m), 1.90–1.85 (2H, m), 1.30–1.10 (3H, m)

[MH⁺] 672

Example 27

N-[3-(dimethylamino)propyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

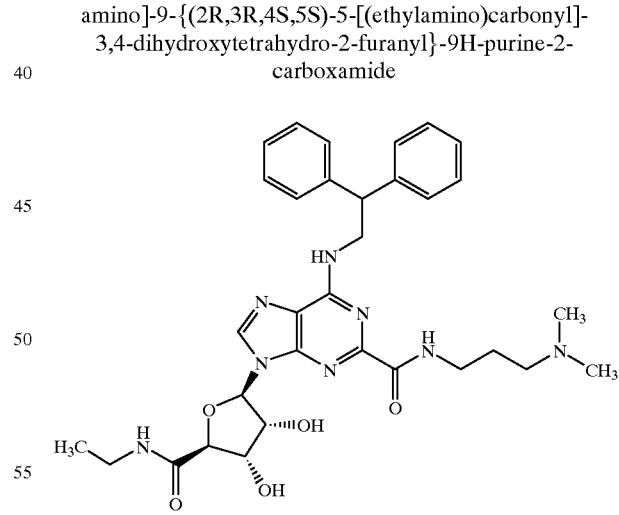

H—NMR (400 MHz, CDCl₃)δ:

δ: 8.90–8.70 (13H, m), 7.60–7.45 (1H, m), 7.45–7.25 (10H, m), 7.00–6.90 (1H, m), 6.00–5.90 (1H, m), 5.20–5.00 (2H, m), 4.65–4.50 (1H, m), 4.45–4.20 (4H, m), 3.60–3.45 (2H, m), 3.45–3.30 (2H, m), 2.45–2.30 (2H, m), 2.15–2.00 (6H, m), 1.85–1.70 (2H, m), 1.25–1.10 (3H, m)

[MH⁺] 617, [MNa⁺] 639

Example 28

6-[(1-benzyl-2-phenylethyl)amino]-9-{(2R,3R,4S,5S)-5-[(ethylamino)carbonyl]-3,4-dihydroxytetrahydro-2-furanyl}-N-[2-(1-piperidinyl)ethyl]-9H-purine-2-carboxamide

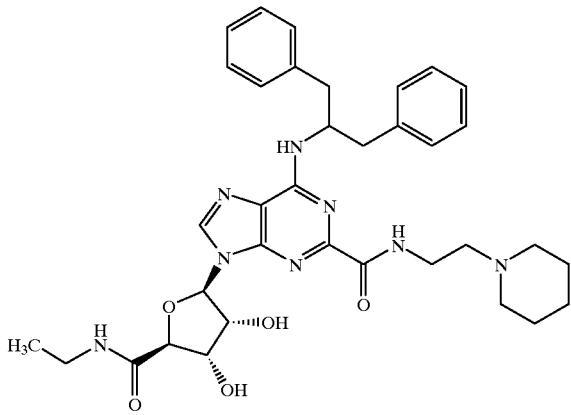

H—NMR (400 MHz, CDCl$_3$)δ:

δ: 8.40 (1H, s), 7.30–7.25 (4H, m), 7.20–7.10 (4H, m), 7.10–7.05 (2H, m), 6.05–6.00 (1H, m), 5.10–5.00 (1H, m), 4.40 (1H, s), 4.40–4.30 (1H, m), 3.60–3.50 (2H, m), 3.40–3.20 (2H, m), 3.10–3.00 (2H, m), 3.00–2.90 (2H, m), 2.65–2.60 (2H, m), 2.60–2.50 (4H, m), 1.70–1.60 (4H, m), 1.55–1.45 (2H, m), 1.05 (3H, t).

[MH$^+$] 657

Example 29

9-{(2R,3R,4S, 5S)-3,4-dihydroxy-5-[(propylamino)carbonyl]tetrahydro-2-furanyl}-6-[(2,2-diphenylethyl)amino]-N-[2-(1-piperidinyl)ethyl]-9H-purine-2-carboxamide

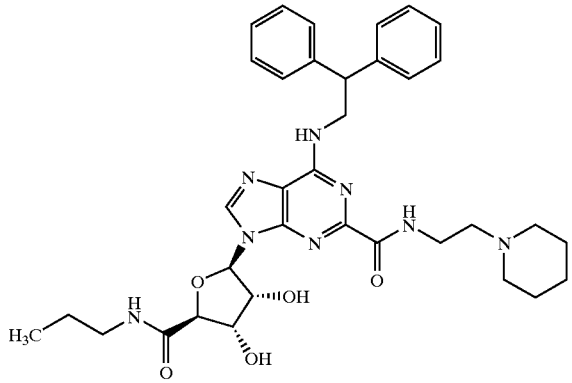

H—NMR (400 MHz, CDCl$_3$)δ:

δ: 8.75 (1H, s), 8.65 (1H, s), 7.50 (1H, s), 7.35–7.15 (10H, m), 6.90 (1H, m), 6.10 (1H, m), 5.05 (1H, s), 4.55 (1H, s), 4.45–4.20 (4H, m), 3.60–3.40 (2H, m), 3.40–3.20 (2H, m), 2.70–2.50 (2H, m), 2.50–2.30 (4H, m), 1.65–1.50 (2H, m), 1.50–1.20 (6H, m), 0.95 (3H, m).

Example 30

6-[(2,2-diphenylethyl)amino]-9-{(2R,3R,4S,5S)-5-[(ethylamino)carbonyl]-3,4-dihydroxytetrahydro-2-furanyl}-N-[2-(1-isopropyl-4-piperidinyl)ethyl]-9H-purine-2-carboxamide

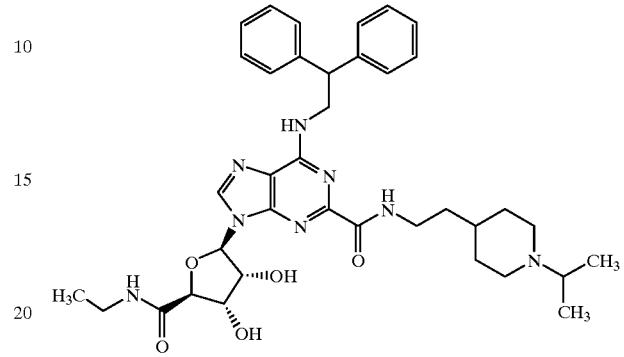

H—NMR (400 MHz, CDCl$_3$)δ:

δ: 8.80–8.70 (1H, m), 8.15–8.05 (1H, m), 7.75–7.55 (1H, m), 7.50–7.40 (1H, m), 7.40–7.20 (10H, m), 7.00–6.90 (1H, m), 5.15–5.00 (2H, m), 4.60–4.50 (1H, m), 4.45–4.15 (4H, m), 3.55–3.30 (4H, m), 2.90–2.80 (2H, m), 2.80–2.60 (1H, m), 2.10–1.95 (2H, m), 1.75–1.50 (4H, m), 1.40–1.15 (6H, m), 1.05–0.95 (6H, m).

Example 31

6-[(2,2-diphenylethyl)amino]-9-{(2R,3R,4S,5S)-5-[(ethylamino)carbonyl]-3,4-dihydroxytetrahydro-2-furanyl}-N-[2-(4-methyl-1-piperidinyl)ethyl]-9H-purine-2-carboxamide

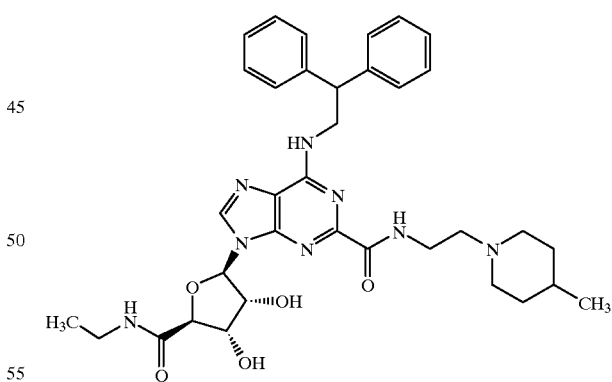

H—NMR (400 MHz, CDCl$_3$)δ:

δ: 8.75 (1H, s), 8.60–8.50 (1H, m), 7.60–7.50 (1H, m), 7.40–7.20 (10H, m), 7.00–6.90 (1H, m), 6.00–5.90 (1H, m), 5.20–5.00 (2H, m), 4.50–4.45 (1H, m), 4.45–4.20 (4H, m), 3.60–3.35 (4H, m), 2.80–2.70 (2H, m), 2.60–2.50 (2H, m), 2.00–1.90 (2H, m), 1.55–1.40 (2H, m), 1.40–1.10 (5H, m), 1.10–0.95 (2H, m), 0.95–0.80 (3H, m).

[MH$^+$] 657

Example 32

6-[(2,2-diphenylethyl)amino]-9-{(2R,3R,4S,5S)-5-[(ethylamino)carbonyl]-3,4-dihydroxytetrahydro-2-furanyl}-N-[2-(4-methoxy-1-piperidinyl)ethyl]-9H-purine-2-carboxamide

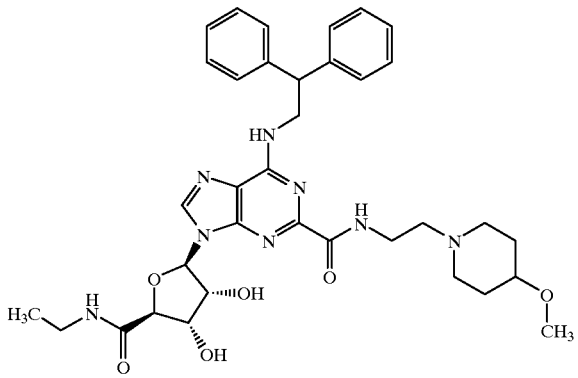

H—NMR (400 MHz, CDCl$_3$)δ:

δ: 8.80 (1H, s), 8.65–8.55 (1H, m), 7.70–7.50 (2H, m), 7.40–7.20 (10H, m), 7.00–6.95 (1H, m), 6.00–5.90 (1H, m), 5.10 (2H, s), 4.55–4.50 (1H, m), 4.40–4.20 (4H, m), 3.55–3.35 (4H, m), 3.20–3.10 (1H, m), 2.70–2.50 (4H, m), 2.25–2.15 (2H, m), 1.75–1.40 (5H, m), 1.25–1.20 (3H, t).

Example 33

6-[(2,2-diphenylethyl)amino]-9-{(2R,3R,4S,5S)-5-[(ethylamino)carbonyl]-3,4-dihydroxytetrahydro-2-furanyl}-N-[(1-methyl-1H-imidazol-4-yl)methyl]-9H-purine-2-carboxamide

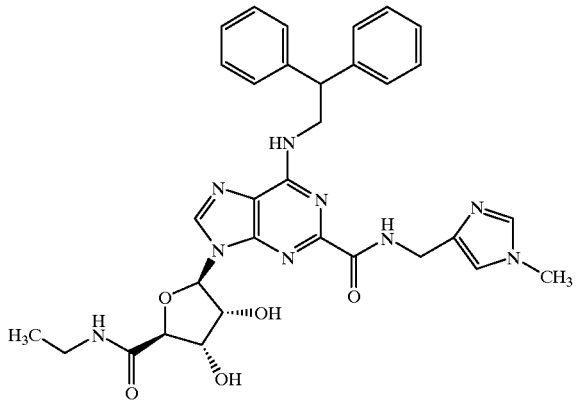

H—NMR (400 MHz, CDCl$_3$)δ:

δ: 8.75 (1H, s), 8.65–8.55 (1H, s), 7.55 (1H, s), 7.35–7.20 (10H, m), 6.95–6.90(1H, m), 6.80 (1H, s), 5.05 (1H, s), 4.60–4.20 (6H, m), 3.60 (3H, s), 3.40–3.25 (2H, m), 1.20–1.10 (3H,

Example 34

6-(Cyclohexylamino)-9-{(2R,3R,4S,5S)-5-[(ethylamino)carbonyl]-3,4-dihydroxytetrahydro-2-furanyl}-N-[2-(1-piperidinyl)ethyl]-9H-purine-2-carboxamide

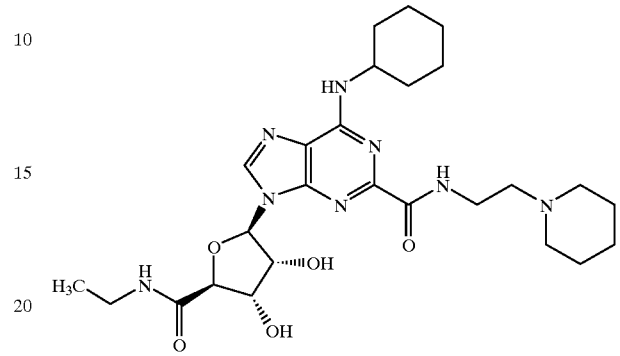

A solution of (2S,3S,4R,5R)-5-[6-(cyclohexylamino)-2-iodo-9H-purin-9-yl]-N-ethyl-3,4-dihydroxytetrahydro-2-furancarboxamide (Preparation 31) (125 mg, 0.24 mmol), 2-(1-piperidinyl)ethylamine (0.14 ml, 0.96 mmol) and tetrakis(triphenylphosphine)palladium(0) (20 mg, 0.024 mmol) in THF (5 ml) was carbonylated at 60° C. and 345 KPa carbon monoxide for 18 hours. Solvent was evaporated under reduced pressure and the residue purified by column chromatography on silica gel eluting with dichloromethane:methanol:concentrated aqueous ammonia (95:5:1, by volume). After evaporation of appropriate fractions the residue was triturated with diethyl ether, filtered and dried to yield the target compound as a beige powder, (77 mg, 58%).

$^1$H—NMR (400 MHz, CDCl$_3$) δ: 8.45 (1H, s), 6.15–6.10 (1H, m), 4.90–4.85 (1H, m), 4.50–4.30 (3H, m), 3.65–3.50 (2H, m), 3.45–3.25 (2H, m), 2.65–2.45 (6H, m), 2.10–2.00 (2H, m), 1.90–1.80 (2H, m), 1.75–1.30 (13H, m), 1.10–1.05 (3H, m).

The following Preparations describe the preparation of certain intermediates used in the preceding Examples.

Preparation 1

2,6-Dichloro-9-tetrahydro-2H-pyran-2-yl-9H-purine

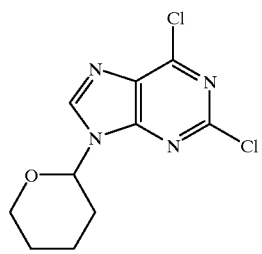

2,6-Dichloro-9H-purine (20 g, 0.11 mol) and 4-toluenesulphonic acid monohydrate (0.2 g) were dissolved in ethyl acetate (300 ml), the mixture was heated to 50° C. and a solution of 2,3-dihydropyran (12.6 ml, 0.14 mol) in ethyl acetate (50 ml) added slowly over 30 minutes. The reaction mixture was then cooled to room temperature, water (100 ml) was added and the pH of the solution was adjusted to 7 by addition of a saturated aqueous solution of sodium hydrogen carbonate. The organic layer was separated, washed sequentially with water and brine, dried over anhydrous magnesium sulphate, filtered and evaporated under reduced pressure. The residue was azeotroped from pentane (×2) to afford the title compound as a slightly impure white solid (30.9 g).

$^1$H—NMR (400 MHz, CDCl$_3$) δ: 8.30 (1H, s), 5.75 (1H, dd), 4.25–4.15 (1H, m), 3.85–3.70 (1H, m), 2.20–1.60 (6H, m).

Preparation 2

2-Chloro-N-(2,2-diphenylethyl)-9-tetrahydro-2H-pyran-2-yl-9H-purin-6-amine

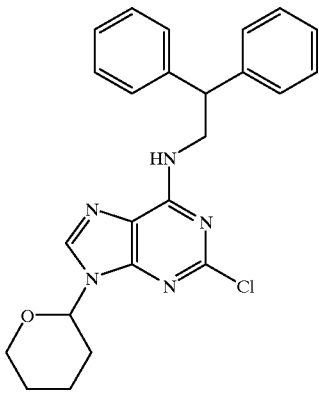

A solution of 2,6-dichloro-9-tetrahydro-2H-pyran-2-yl-9H-purine (Preparation 1) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture was heated at reflux for 3 hours. The solvent was removed under reduced pressure and the residue was azeotroped from ethyl acetate. The residue was then purified by column chromatography on silica gel eluting with a gradient system of ethyl acetate:hexane (40:60 by volume) gradually changing to ethyl acetate:hexane (60:40 by volume) to afford the title compound as a foam (49.7 g).

$^1$H—NMR (400 MHz, CDCl$_3$)δ: 7.95–7.75 (1H, br s), 7.35–7.15 (10H, m), 5.80–5.70 (1H, br s), 5.65 (1H, d), 4.35 (1H, m), 4.30–4.18 (1H, br s), 4.10 (1H, d), 3.70 (1H, t), 2.05–1.95 (2H, m), 1.95–1.80 (1H, m), 1.80–1.55 (3H, m).

Preparation 3

6-[(2,2-Diphenylethyl)amino]-9-tetrahydro-2H-pyran-2-yl-9H-purine-2-carbonitrile

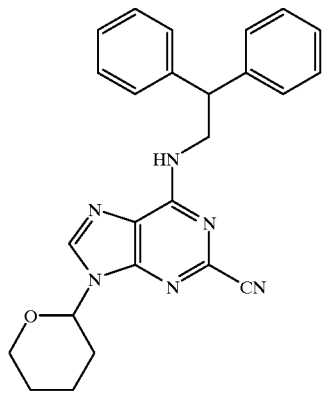

A solution of 2-chloro-N-(2,2-diphenylethyl)-9-tetrahydro-2H-pyran-2-yl-9H-purin-6-amine (Preparation 2) (1.0 g, 2.31 mmol), zinc cyanide (0.162 g, 1.38 mmol), triethylamine (0.28 g, 2.77 mmol) and tetrakis(triphenylphosphine)-palladium(0) (0.133 g, 0.12 mmol) in N,N-dimethylformamide (3 ml) was heated under a nitrogen atmosphere at 100° C. for 6 hours. The reaction mixture was allowed to cool and partitioned between ethyl acetate (100 ml) and 2 M sodium hydroxide solution (100 ml). The organic layer was separated, dried over anhydrous magnesium sulphate and evaporated under reduced pressure. The resulting 1:1 mixture of 6-[(2,2-diphenylethyl)amino]-9-tetrahydro-2H-pyran-2-yl-9H-purine-2-carbonitrile and 6-[(2,2-diphenylethyl)amino]-9H-purine-2-carbonitrile (Preparation 8) were separated by column chromatography on silica gel eluting with a gradient system of ethyl acetate:hexane (40:60 by volume) gradually changing to ethyl acetate:hexane (60:40 by volume) to give the title compound as a white solid (0.4 g).

$^1$H—NMR (400 MHz, CDCl$_3$) δ: 8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

Preparation 4

Methyl 6-[(2,2-diphenylethyl)amino]-9-tetrahydro-2H-pyran-2-yl-9H-purine-2-carboxylate

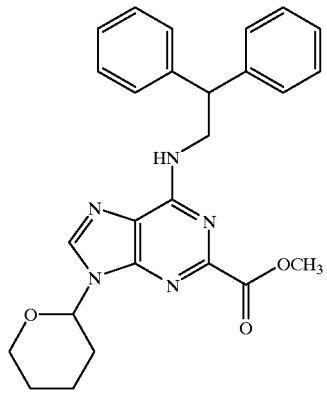

A suspension of 6-[(2,2-diphenylethyl)amino]-9-tetrahydro-2H-pyran-2-yl-9H-purine-2-carbonitrile (Preparation 3) (1.00 g, 2.36 mmol) in methanol (20 ml) was treated with sodium methoxide (0.14 g, 2.59 mmol) and the resulting mixture was heated at reflux under a nitrogen atmosphere for 20 hours. TLC analysis showed that some starting material still remained therefore further sodium methoxide (64 mg, 1.18 mmol) was added and the mixture was heated at reflux under a nitrogen atmosphere for a further hour. The mixture was then cooled to room temperature and the solvent was removed under reduced pressure. Tetrahydrofuran (30 ml) and water (10 ml) were added to the residue and the pH was adjusted to 4 by addition of acetic acid (1 ml). This mixture was heated at reflux for 1 hour. TLC analysis showed that some starting material still remained and therefore further acetic acid (0.5 ml) was added and heating at reflux continued for 18 hours. The reaction was cooled to room temperature and partitioned between ethyl acetate and a saturated aqueous solution of sodium hydrogen carbonate. The organic phase was separated, washed with brine, dried over anhydrous magnesium sulphate, filtered and evaporated under reduced pressure. The residue was purified by column chromatography on silica gel eluting with dichloromethane: methanol (98.5:1.5 by volume) to afford the title compound (521 mg).

$^1$H—NMR (400 MHz, CDCl$_3$) δ: 8.05 (1H, br s), 7.37–7.18 (10H, m), 5.84 (2H, m), 4.40 (3H, m), 4.14 (1H, d), 4.00 (3H, s), 3.78 (1H, t), 2.17–1.60 (6H, m).

LRMS (thermospray): m/z [MH$^+$] 458, [MNa$^+$] 480.

Preparation 5

6-[(2,2-Diphenylethyl)amino]-N-[2-(1-piperidinyl)ethyl]-9-tetrahydro-2H-pyran-2-yl-9H-purine-2-carboxamide

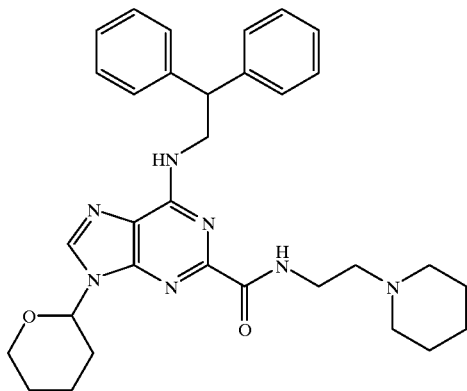

Methyl 6-[(2,2-diphenylethyl)amino]-9-tetrahydro-2H-pyran-2-yl-9H-purine-2-carboxylate (Preparation 4) (100 mg, 0.22 mmol) and 1-(2-aminoethyl)piperidine (0.31 ml, 2.19 mmol) were heated together at 130° C. for 2 hours. The excess amine was removed under reduced pressure and the residue was purified by column chromatography on silica gel eluting with dichloromethane methanol (95:5 by volume) to afford the title compound as a yellow foam (104 mg).

$^1$H—NMR (400 MHz, CDCl$_3$) δ: 8.43 (1H, br m), 8.00 (1H, br s), 7.17–7.36 (10H, m), 5.94 (1H, d), 5.80 (1H, br m), 4.37 (3H, m), 4.33 (1H, d), 3.78 (1H, t), 3.57 (2H, m), 2.55 (2H, m), 2.40 (4H, br m), 1.65–2.17 (6H, m), 1.26–1.33 (6H, br m).

LRMS (thermospray): m/z [MH$^+$] 554.

Preparation 6

6-[(2,2-Diphenylethyl)amino]-N-[2-(1-piperidinyl)ethyl]-9H-purine-2-carboxamide

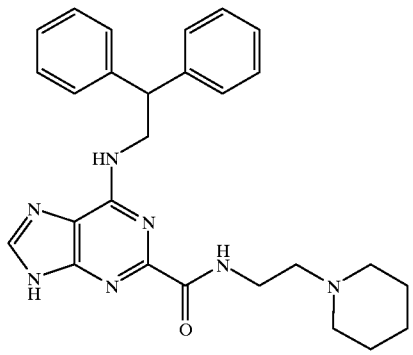

A solution of 6-[(2,2-diphenylethyl)amino]-N-[2-(1-piperidinyl)ethyl]-9-tetrahydro-2H-pyran-2-yl-9H-purine-2-carboxamide (Preparation 5) (420 mg, 0.76 mmol) in ethanol (20 ml) was treated with hydrochloric acid (2 M, 0.9 ml). The mixture was heated at reflux for 30 minutes after which time a white precipitate had formed. The mixture was cooled to room temperature and the solvent was removed under reduced pressure. The residue was partitioned between dichloromethane and 10% weight by volume aqueous ammonia. The organic phase was separated, dried over anhydrous magnesium sulphate, filtered and evaporated under reduced pressure to afford the title compound as a white solid (319 mg).

$^1$H—NMR (400 MHz, CDCl$_3$) δ: 8.57 (1H, br m), 8.30 (1H, s), 7.40–7.20 (10H, m), 5.93 (1H, br s), 4.39 (3H, m), 3.62 (2H, m), 2.56 (2H, t), 2.40 (4H, br m), 1.47–1.24 (6H, br m).

LRMS (thermospray): m/z [MH$^+$] 470, [MNa$^+$] 492.

Preparation 7

(2R,3R,4R,5S)-4-(Benzoyloxy)-2-[6-[(2,2-diphenylethyl)amino]-2-({[2-(1-piperidinyl)-ethyl]amino}carbonyl)-9H-purin-9-yl]-5-[(ethylamino)carbonyl]tetrahydro-3-furanyl benzoate

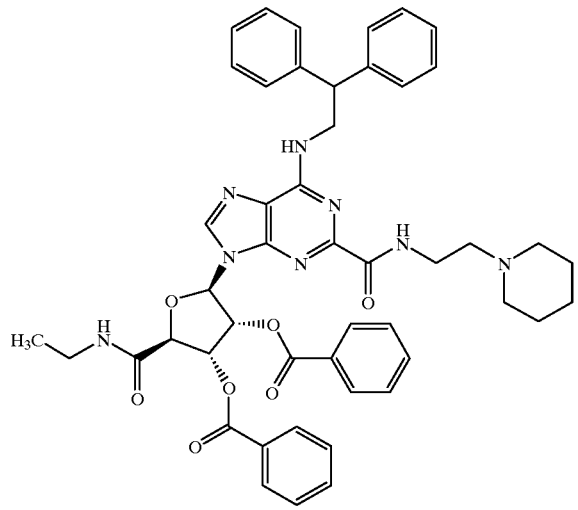

A suspension of 6-[(2,2-diphenylethyl)amino]-N-[2-(1-piperidinyl)ethyl]-9H-purine-2-carboxamide (Preparation 6)

(100 mg, 0.21 mmol) in 1,1,1-trichloroethane (2 ml) was treated with N,O-bis(trimethylsilyl)acetamide (0.21 ml, 0.85 mmol). The mixture was heated at reflux for 90 minutes. The solution was allowed to cool to room temperature and the solvent was removed under reduced pressure. The residue was treated with a solution of (2S,3R,4R,5R)-and (2S,3R,4R,5S)-5-(acetyloxy)-4-(benzoyloxy)-2-[(ethylamino)carbonyl] tetrahydro-3-furanyl benzoate (Preparation 15) (111 mg, 0.25 mmol) in anhydrous toluene (2 ml) and trimethylsilyl trifluoromethanesulfonate (0.05 ml, 0.30 mmol). The resulting solution was then heated at 90° C. under a nitrogen atmosphere for 1 hour. TLC analysis showed that some starting material still remained and therefore further trimethylsilyl trifluoromethanesulfonate (0.05 ml, 0.30 mmol) was added and the heating was continued for 2 hours. Again TLC analysis showed that some starting material still remained therefore further trimethylsilyl trifluoromethanesulfonate (0.025 ml, 0.15 mmol) was added and the heating was continued for a further hour. The mixture was cooled to room temperature, diluted with ethyl acetate (20 ml) and washed with a saturated aqueous solution of sodium hydrogen carbonate. The organic layer was separated, dried over anhydrous magnesium sulphate, filtered and evaporated under reduced pressure. The residue was purified by column chromatography on silica gel eluting with dichloromethane:methanol (90:10 by volume) to afford the title compound as a foam (109 mg).

$^1$H—NMR (400 MHz, CDCl$_3$) δ: 8.35 (1H, br m), 8.06 (3H, d), 7.93 (2H, d), 7.69–7.18 (15H, m), 6.44 (1H, d), 6.23 (2H, br m), 5.91 (1H, br m), 4.92 (1H, d), 4.37 (3H, m), 3.53 (4H, m), 2.60 (2H, br m), 2.44 (4H, br m), 1.40 (6H, m), 1.13 (3H, t).

LRMS (thermospray): m/z [MH$^+$] 851.

Preparation 8

6-[(2,2-Diphenylethyl)amino]-9H-purine-2-carbonitrile

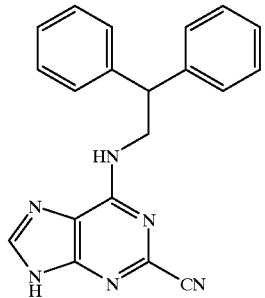

A solution of 6-[(2,2-diphenylethyl)amino]-9-tetrahydro-2H-pyran-2-yl-9H-purine-2-carbonitrile (Preparation 3) (17 g, 40.1 mmol) in ethanol (850 ml), was treated with 2 M aqueous hydrochloric acid (50 ml) and the mixture was stirred at room temperature for 24 hours. The solvent was removed under reduced pressure, the residue was dissolved in ethanol and the solvent was again removed under reduced pressure. The residue was triturated with diethyl ether, filtered, washed with diethyl ether and pentane and dried to afford the title compound as a solid (13.6 g).

$^1$H—NMR (400 MHz, DMSO-d$_6$) δ: 8.30 (1H, s), 8.20–8.05 (1H, br s), 7.40–7.10 (10H, m), 4.60–4.40 (1.4H, m), 4.20–4.00 (1.6H, m).

LRMS (thermospray): m/z [MH$^+$] 341.

Preparation 9

Methyl 6-[(2,2-diphenylethyl)amino]-9H-purine-2-carboxylate

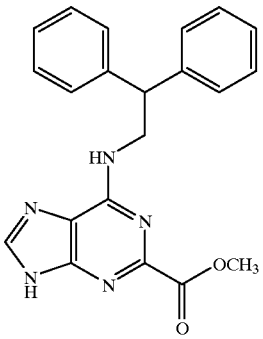

A solution of 6-[(2,2-diphenylethyl)amino]-9H-purine-2-carbonitrile (Preparation 8) (5.0 g, 14.7 mmol) and sodium methoxide (4.0 g, 74.1 mmol) in methanol (300 ml) was heated under reflux for 24 hours. Further sodium methoxide (2.0 g, 37 mmol) and methanol (100 ml) were then added and heating was continued for a further 24 hours. The reaction mixture was allowed to cool and the solvent was removed under reduced pressure. The residue was dissolved in THF (375 ml), 2 M hydrochloric acid (125 ml) was added and the mixture was stirred at room temperature for 24 hours. The THF was removed under reduced pressure and the suspension was adjusted to pH 7 with saturated aqueous sodium bicarbonate solution. Ethyl acetate (100 ml) was then added and the white solid consisting mainly of the desired product was filtered, washed with a little water and ethyl acetate and dried. Purification by column chromatography on silica gel eluting with a gradient system of dichloromethane: methanol (90:10 by volume) gradually changing to dichloromethane: methanol (75:25 by volume) afforded the title compound as a white solid (1.25 g). Evaporation of the ethyl acetate filtrate returned 2.6 g of the starting material.

$^1$H—NMR (400 MHz, CDCl3) δ: 12.40 (1H, br s), 8.05 (1H, s), 7.55 (1H, s), 7.30–7.20 (10H, m), 4.80 (2H, m), 4.75 (1H, m), 3.80 (3H, s).

LRMS (thermospray): m/z [MH$^+$] 375.

Preparation 10

Methyl 9-{(2R,3R,4R,5S)-3,4-bis(benzoyloxy)-5-[(ethylamino)carbonyl]-tetrahydro-2-furanyl}-6-[(2,2-diphenylethyl)amino]-9H-purine-2-carboxylate

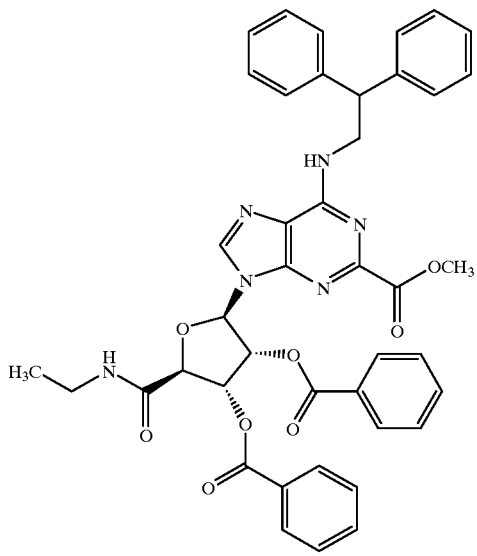

A suspension of methyl 6-[(2,2-diphenylethyl)amino]-9H-purine-2-carboxylate (Preparation 9) (440 mg, 1.18 mmol) in 1,1,1-trichloroethane (25 ml) was treated with N,O-bis(trimethylsilyl)acetamide (1.7 ml, 6.95 mmol). The mixture was heated at reflux for one hour. The solution was allowed to cool to room temperature and the solvent was removed under reduced pressure. The residue was treated with a solution of (2S,3R,4R,5R)- and (2S,3R,4R,5S)-5-(acetyloxy)-4-(benzoyloxy)-2-[(ethylamino)carbonyl] tetrahydro-3-furanyl benzoate (Preparation 15) (620 mg, 1.4 mmol) in anhydrous toluene (25 ml) and trimethylsilyl trifluoromethanesulfonate (0.26 ml, 1.42 mmol). The resulting solution was then heated at 110° C. under a nitrogen atmosphere for 2.5 hours. The mixture was cooled to room temperature, diluted with ethyl acetate (200 ml) and washed with a saturated aqueous solution of sodium hydrogen carbonate. The organic layer was separated, dried over anhydrous magnesium sulphate, filtered and evaporated under reduced pressure. The residue was purified by column chromatography on silica gel eluting with dichloromethane:ethyl acetate (5:1 by volume) then dichloromethane:ethyl acetate (1:1 by volume) to afford the title compound as a foam (540 mg).

$^1$H—NMR (400 MHz, CDCl$_3$)δ: 8.10 (3H, m), 7.80 (2H, d), 7.60 (1H, m), 7.50–7.40 (4H, m), 7.35–7.20 (16H, m), 6.40 (1H, m), 6.20 (2H, m), 5.90 (1H, m), 4.90 (1H, d), 4.40 (3H, m), 4.00 (3H, s), 3.55 (1H, m), 3.35 (1H, m), 1.15 (3H, t).

LRMS (thermospray): m/z [MNa$^+$] 777.

Preparation 11

Methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate

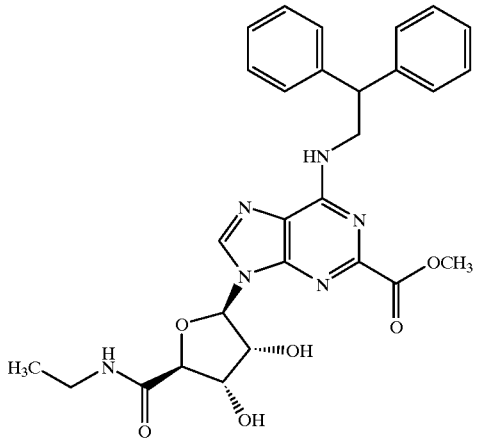

A solution of methyl 9-{(2R,3R,4R,5S)-3,4-bis(benzoyloxy)-5-[(ethylamino)carbonyl]-tetrahydro-2-furanyl}-6-[(2,2-diphenylethyl)amino]-9H-purine-2-carboxylate (Preparation 10) (3.4 g, 4.5 mmol) and sodium carbonate (50 mg) in dry methanol (60 ml) was stirred at room temperature for four hours. The solvent was removed under reduced pressure and the residue was taken up in a mixture of dichloromethane:methanol (95:5 by volume, 60 ml). Inorganic salts were filtered off and the filtrate was evaporated under reduced pressure. The residue was triturated with ether, filtered off and dried to yield the target compound as a white solid (2.4 g).

$^1$H—NMR (400 MHz, d$_6$-DMSO) δ: 8.60 (1H, m), 8.15 (2H, br s), 7.40–7.15 (10H, m), 6.00 (1H, br m), 5.60 (1H, br s), 5.50 (1H, br s), 4.60–4.40 (3H, m), 4.30 (1H, s), 4.10–4.05 (2H, m), 4.00–3.80 (3H, m), 3.20 (2H, m), 1.00 (3H, t).

LRMS (thermospray): m/z [MH$^+$] 547.

Preparation 12

(3aS,4S,6R,6aR)-N-Ethyl-6-methoxy-2,2-dimethyltetrahydrofuro[3,4-d][1,3]dioxole-4-carboxamide

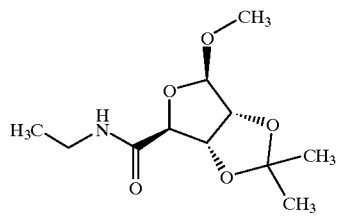

Oxalyl chloride (14.0 ml, 160 mmol) was added dropwise to a stirred solution of (3aR,4S,6R,6aR)-6-methoxy-2,2-dimethyltetrahydrofuro[3,4-d][1,3]dioxole-4-carboxylic acid (*J. Am. Chem. Soc.*, 1958, 80, 5168) (23.30 g, 107 mmol) in anhydrous dichloromethane (120 ml) and N,N-dimethylformamide (2 drops) and the mixture was stirred at room temperature for 3 hours until gas evolution had ceased. TLC analysis showed that some starting material still remained and so further N,N-dimethylformamide (2 drops) was added and stirring was continued for 1 hour. The solvent was removed under reduced pressure and the residue was azeotroped with anhydrous dichloromethane (×2). The residue was then dissolved in anhydrous dichloromethane (200 ml) and the solution was treated dropwise with ethylamine (2 M in tetrahydrofuran, 140 ml, 280 mmol). This solution was left at room temperature for 48 hours. Diethyl ether (250 ml) was added and the mixture was stirred for 15 minutes. The mixture was filtered and the solvent was removed from the filtrate under reduced pressure. The residue was purified by column chromatography on silica gel eluting with a gradient system of dichloromethane:ethyl acetate (100:0 by volume) gradually changing to dichloromethane:ethyl acetate (44:66by volume) to afford the title compound as a yellow solid (24.70 g).

$^1$H—NMR (400 MHz, CDCl$_3$) δ: 6.53 (1H, br m), 5.12 (1H, dd), 5.07 (1H, d), 4.60 (1H, d), 4.54 (1H, dd), 3.46 (3H, s), 3.32 (2H, m), 1.51 (3H, s), 1.34 (3H, s), 1.15 (3H, t).

LRMS (thermospray): m/z [MH$^+$] 246.

Preparation 13

(2S,3S,4R,5R)- and (2S,3S,4R,5S)-N-Ethyl-3,4-dihydroxy-5-methoxytetrahydro-2-furancarboxamide

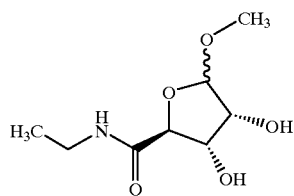

A solution of (3aS,4S,6R,6aR)-N-ethyl-6-methoxy-2,2-dimethyltetrahydrofuro[3,4-d][1,3]dioxole-4-carboxamide (Preparation 12) (24.60 g, 100 mmol) and pyridinium p-toluenesulphonate (2.50 g, 10 mmol) in methanol (500 ml) was heated at reflux for 18 hours. NMR analysis showed that some starting material still remained. The solvent was removed under reduced pressure. The residue was dissolved in methanol (500 ml) and heated under reflux for 8 hours. NMR analysis showed that some starting material still remained therefore the solvent was removed under reduced pressure once more. The residue was dissolved in methanol (500 ml) and the resulting solution was heated under reflux for 24 hours. The solvent was then removed under reduced pressure and the residue was azeotroped with dichloromethane (×3) to afford the title compound as an oil (20.50 g).

$^1$H—NMR (400 MHz, CDCl$_3$) δ: 6.58 (1H, br m), 4.99 (0.25H, d), 4.94 (0.75H, d), 4.46 (0.25H, d), 4.37 (1.5H, m), 4.24 (0.25H, dd), 4.05 (1H, m), 3.52 (0.75H, s), 3.47 (2.25H, s), 3.30 (2H, m), 1.16 (3H, m)

Preparation 14

(2S,3R,4R,5S)- and (2R,3R,4R,5S)-4-(Benzoyloxy)-5-[(ethylamino)carbonyl]-2-methoxytetrahydro-3-furanyl benzoate

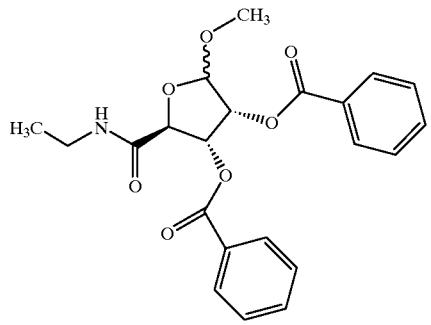

A solution of benzoyl chloride (30.0 ml, 259 mmol) in dichloromethane (100 ml) was added slowly to a solution of (2S,3S,4R,5R)- and (2S,3S,4R,5S)-N-ethyl-3,4-dihydroxy-5-methoxytetrahydro-2-furancarboxamide (Preparation 13) (20.50 g, 100 mmol) and pyridine (33.0 ml, 409 mmol) in dichloromethane (400 ml) and the resulting mixture was stirred at room temperature for 18 hours. The solvent was removed under reduced pressure and the residue was partitioned between diethyl ether and hydrochloric acid (1 M, 300 ml). The layers were separated and the aqueous layer was re-extracted with diethyl ether. The organic layers were combined, washed sequentially with water and brine, dried over anhydrous magnesium sulphate, filtered and evaporated under reduced pressure. The residue was purified by column chromatography on silica gel eluting with a gradient system of dichloromethane:diethyl ether (95:5 by volume) gradually changing to dichloromethane:diethyl ether (80:20 by volume) to afford the title compound as an oil and as a mixture of α and β anomers (37.0 g).

$^1$H—NMR (400 MHz, CDCl$_3$) δ: 8.16 (0.5H, d), 7.95 (1.5H, d), 7.88 (1.5H, d), 7.81 (0.5H, d), 7.66–7.25 (6H, m), 6.65 (1H, br m), 5.88 (1H, m), 5.60 (0.75H, dd), 5.46 (0.25H, d), 5.23 (0.75H, d), 5.17 (0.25H, t), 4.80 (1H, m), 3.59 (2.25H, s), 3.49 (0.75H, s), 3.39 (2H, m), 1.23 (3H, t)

Preparation 15

(2S,3R,4R,5R)- and (2S,3R,4R,5S)-5-(Acetyloxy)-4-(benzoyloxy)-2-[(ethylamino)carbonyl]tetrahydro-3-furanyl benzoate

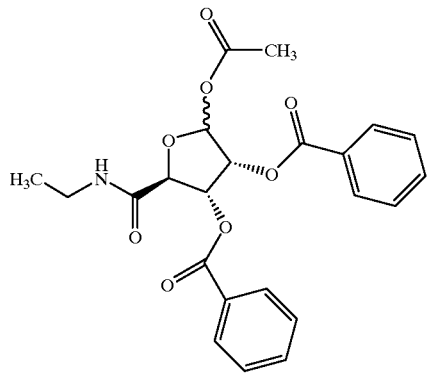

A solution of (2S,3R,4R,5S)- and (2R,3R,4R,5S)-4-(benzoyloxy)-5-[(ethylamino)carbonyl]-2- methoxytetrahydro-3-furanyl benzoate (Preparation 14) (37.0 g, 89.6 mmol) in a mixture of acetic acid (330 ml, 5.77 mol) and acetic anhydride (67 ml, 709 mmol) was cooled to −10° C. and treated dropwise with hydrochloric acid (12 N, 7.0 ml, 132 mmol). The mixture was stirred for 18 hours, during which time it was allowed to warm up to room temperature. After cooling the mixture to 0° C., it was diluted with water (1000 ml) and then extracted with ethyl acetate (3×500 ml). The organic layers were combined, washed sequentially with water, a saturated aqueous solution of sodium hydrogen carbonate and brine, dried over anhydrous magnesium sulphate, filtered and evaporated under reduced pressure. The residue was purified by column chromatography on silica gel eluting with a gradient system of diethyl ether:pentane (66:44 by volume) gradually changing to diethyl ether:pentane (100:0 by volume). The residue was further purified by column chromatography on silica gel eluting with a gradient system of dichloromethane:diethyl ether (95:5 by volume) gradually changing to dichloromethane:diethyl ether (90:10 by volume) to afford the title compound as a mixture of α- and β-anomers (15.40 g).

$^1$H—NMR (400 MHz, CDCl$_3$) δ: 8.12 (0.8H, d), 7.97 (1.2H, d), 7.92 (1.2H, d), 7.79 (0.8H, d), 7.65–7.24 (6H, m), 6.73 (0.4H, d), 6.62 (0.4H, br m), 6.46 (0.6H, br m), 6.42 (0.6H, d), 6.07 (0.4H, dd), 5.95 (0.6H, t), 5.72 (0.6H, d), 5.44 (0.4H, t), 4.94 (0.4H, d), 4.86 (0.6H, d), 3.36 (2H, m), 2.17 (1.8H, s), 2.10 (1.2H, s), 1.20 (3H, m).(2S,3R,4R,5R)- and (2S,3R,4R,5S)-5-(Acetyloxy)-4-(benzoyloxy)-2-[(propylamino)carbonyl]tetrahydro-3-furanyl benzoate were prepared in an analogus manner.

Preparation 16

2-[2-(4-Isopropyl-1-piperidinyl)ethyl]-1H-isoindole-1,3(2H)-dione

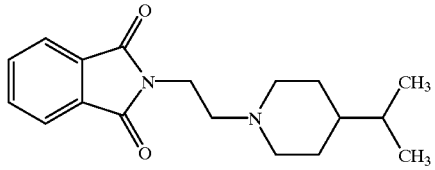

A solution of 4-isopropylpiperidine (3.3 g, 20.2 mmol) and 2-bromoethylphthalimide (5.4 g, 21.3 mmol) in acetonitrile (100 ml) was treated with potassium carbonate (5.9 g, 45.4 mmol), heated under reflux for 2.5 hours and then stirred at room temperature overnight. The solvent was removed under reduced pressure and the residue was partitioned between ethyl acetate (100 ml) and water (100 ml). The organic layer was separated and the aqueous layer extracted with further ethyl acetate (100 ml). The combined organic extracts were dried over sodium sulfate and the solvent was removed under reduced pressure. The resulting oil was purified by column chromatography on silica gel eluting with a gradient system of dichloromethane:diethyl ether (50:50 by volume) changing to pure diethyl ether to afford the title compound (3.39).

$^1$H—NMR (400 MHz, CDCl$_3$) δ: 7.80 (2H, m), 7.70 (2H, m), 3.80 (2H, t), 3.00 (2H, m), 2.60 (2H, t), 1.95 (2H, m), 1.60 (2H, m), 1.40 (1H, m), 1.20 (2H, dq), 0.95 (1H, m), 0.80 (6H, d).

LRMS (thermospray): m/z [MH$^+$] 301.

Preparation 17

2-(4-Isopropyl-1-piperidinyl)ethylamine

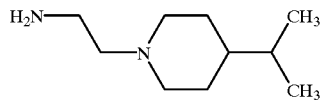

A solution of (2-[2-(4-isopropyl-1-piperidinyl)ethyl]-1H-isoindole-1,3(2H)-dione (Preparation 16) (3.2 g, 10.6 mmol) in a 33% solution of methylamine in ethanol (60 ml) was heated at reflux for three hours. The solvent was removed under reduced pressure, further ethanol (60 ml) was added and the solvent was again removed under reduced pressure. The residue was suspended in dichloromethane (100 ml) and the solid was filtered off and washed with further dichloromethane (100 ml). The filtrate was evaporated under reduced pressure and purified by column chromatography on silica gel eluting with dichloromethane:methanol:concentrated aqueous ammonia (90:10:1 by volume) to give a colourless oil. Bulb to bulb distillation (150–160° C., 30 mmHg) yielded the title compound (1.0 g).

$^1$H—NMR (400 MHz, CDCl$_3$) δ: 2.90 (2H, m), 2.80 (2H, t), 2.40 (2H, t), 1.95 (2H, m), 1.65 (2H, m), 1.40 (1H, m), 1.30–1.20 (4H, m), 1.00 (1H, m), 0.85 (6H, d).

LRMS (thermospray): m/z [MH$^+$] 171.

Preparation 18

(2R,3R,4S,5S)-2-(2-Amino-6-chloro-9H-purin-9-yl)-4-(benzoyloxy)-5-[(ethylamino)carbonyl]-tetrahydro-3-furanyl benzoate

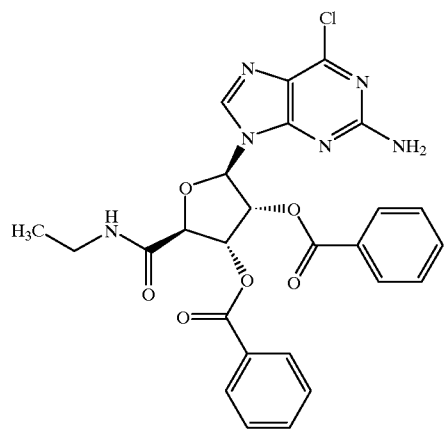

A suspension of 2-amino-6-chloropurine (4.60 g, 27.13 mmol) in 1,1,1-trichloroethane (230 ml) was treated with N,O-bis(trimethylsilyl)acetamide (20 ml, 81.4 mmol). The mixture was heated at reflux for 6 hours. The solution was allowed to cool to room temperature and the solvent was removed under reduced pressure. The residue was treated with a solution of (2S,3R,4R, 5R)- and (2S,3R,4R, 5S)-5-(acetyloxy)-4-(benzoyloxy)-2-[(ethylamino)carbonyl] tetrahydro-3-furanyl benzoate (Preparation 15) (14.39 g, 32.6 mmol) in anhydrous toluene (230 ml) and trimethylsilyl trifluoromethanesulfonate (20 ml, 108.5 mmol). The resulting solution was then heated at 90° C. under a nitrogen atmosphere for 90 minutes. The mixture was cooled to room temperature, diluted with ethyl acetate (250 ml) and washed with a saturated aqueous solution of sodium hydrogen carbonate (350 ml) then brine (350 ml). The organic layer was separated, dried over anhydrous magnesium sulfate, filtered and evaporated under reduced pressure. The residue was purified by column chromatography on silica gel eluting with dichloromethane:methanol (98:2 by volume) to afford the title compound as a white foam (8.1 g).

$^1$H—NMR (400 MHz, CDCl$_3$) δ: 8.10–7.95 (3H, m), 7.80 (2H, m), 7.50–7.30 (6H, m), 6.90 (1H, m), 6.40–6.20 (3H, m), 5.20 (2H, br s), 4.90 (1H, m), 3.45 (1H, m), 3.30 (1H, m), 1.15 (3H, t).

LRMS m/z [MH$^+$] 552.

Preparation 19

(2R,3R,4S,5S)-4-(Benzoyloxy)-2-(6-chloro-2-iodo-9H-purin-9-yl)-5-[(ethylamino)carbonyl]-tetrahydro-3-furanyl benzoate

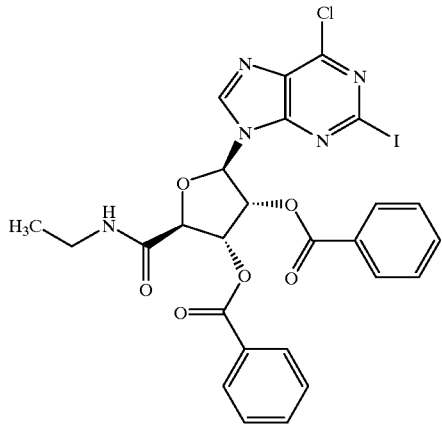

n-Butyl nitrite (4.65 ml, 39.7 mmol) was added to a suspension of (2R,3R,4S,5S)-2-(2-amino-6-chloro-9H-purin-9-yl)-4-(benzoyloxy)-5-[(ethylamino)carbonyl]-tetrahydro-3-furanyl benzoate (Preparation 18) (8.10 g, 14.7 mmol), iodine (3.73 g, 14.7 mmol), copper(I) iodide (6.16 g, 32.3 mmol) and diiodomethane (12.55 ml, 155.8 mmol) in THF (100 ml) and the mixture was heated at reflux for 2.5 hours. The solution was allowed to cool to room temperature and the solvent was removed under reduced pressure. The residue was partitioned between aqueous sodium metabisulfite solution (5%, 100 ml) and dichloromethane (100 ml). The organic layer was separated, filtered through arbacel, dried (MgSO$_4$) and solvent evaporated under reduced pressure. The residue was purified by column chromatography on silica gel eluting with dichloromethane:methanol (99:1 by volume) to afford the title compound as a yellow foam (7.55 g, 78%).

$^1$H—NMR (400 MHz, CDCl$_3$) δ: 8.55 (1H, s), 8.05 (2H, m), 7.80 (2H, m), 7.65–7.30 (6H, m), 6.75 (1H, m), 6.50 (1H, m), 6.10–6.00 (2H, m), 4.90 (1H, m), 3.60–3.40 (2H, m), 1.25 (3H, t).

LRMS : m/z [MNa$^+$] 684.

Preparation 20

(2R,3R,4S, 5S)-4-(Benzoyloxy)-2-{6-[(2-benzyl-3-phenylpropyl)amino]-2-iodo-9H-purin-9-yl}-5-[(ethylamino)carbonyl]tetrahydro-3-furanyl benzoate

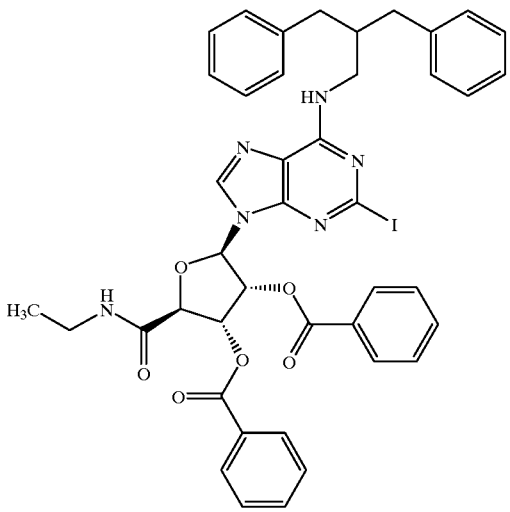

A solution of ((2R,3R,4S,5S)-4-(benzoyloxy)-2-(6-chloro-2-iodo-9H-purin-9-yl)-5-[(ethylamino)carbonyl]-tetrahydro-3-furanyl benzoate (Preparation 19) (0.25 g, 0.38 mmol) and 2-benzyl-3-phenylpropylamine (0.16 g, 0.76 mmol) in isopropanol (10 ml) was stirred at room temperature for 48 hours. Solvent was removed under reduced pressure and the residue purified by column chromatography on silica gel eluting with dichloromethane:methanol (99:1 by volume) to afford the title compound as a yellow foam (0.26 g, 83%).

$^1$HNMR (400 MHz, CDCl$_3$) δ: 8.00 (2H, m), 7.80 (3H, m), 7.60–7.40 (5H, m), 7.35–7.15 (9H, m), 6.25 (1H, m), 6.15–6.05 (2H, m), 5.75 (1H, br s), 4.90–4.80 (2H, m), 3.65 (1H, m), 3.50 (1H, m), 3.00–2.85 (4H, m), 1.20 (3H, t).

LRMS: m/z [MH$^+$] 837.

Preparation 21

(2R,3R,4S, 5)-4-(Benzoyloxy)-2-(6-{[2,2-bis(3-phenyl)ethyl]amino}-2-iodo-9H-purin-9-yl)-5-[(ethylamino)carbonyl]tetrahydro-3-furanyl benzoate

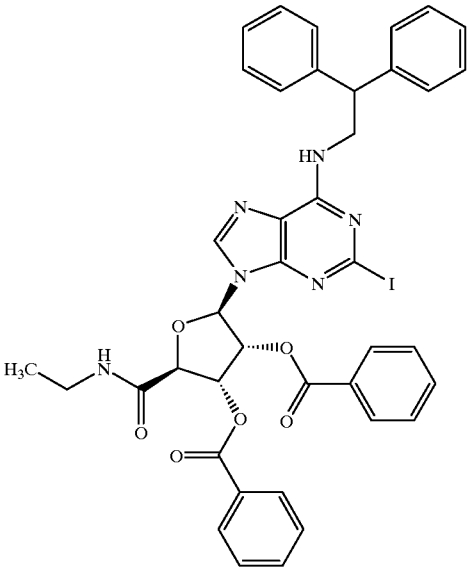

Prepared from ((2R,3R,4S,5S)-4-(benzoyloxy)-2-(6-chloro-2-iodo-9H-purin-9-yl)-5-[(ethylamino)carbonyl]-tetrahydro-3-furanyl benzoate (Preparation 19) and 2,2-bis(phenyl)ethylamine by the same method as Preparation 20. The title compound was obtained as a yellow foam.

¹H—NMR (400 MHz, CDCl₃) δ: 8.05 (2H, m), 7.80 (3H, m), 7.60–7.40 (5H, m), 7.35–7.15 (9H, m), 6.25 (1H, m), 6.15–6.05 (2H, m), 5.75 (1H, br s), 4.90 (1H, m), 4.40 (1H, m), 4.25 (1H, br s), 3.65 (1H, m), 3.50 (1H, m), 1.25 (3H, t).

LRMS: m/z [MH⁺] 823.

Preparation 22

(2R,3R,4S,5S)-4-(Benzoyloxy)-5-[(ethylamino)carbonyl]-2-{6-[(1-ethylpropyl)amino]-2-iodo-9H-purin-9-yl}tetrahydro-3-furanyl benzoate

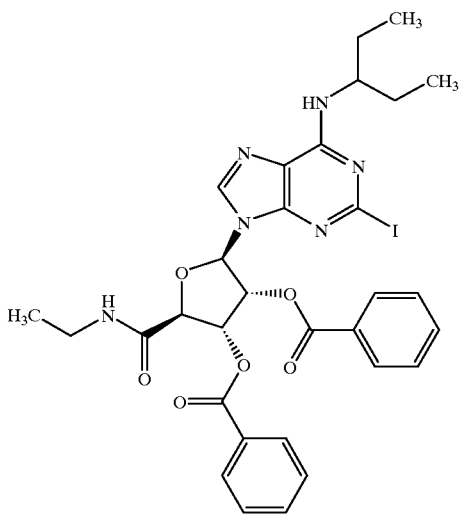

Prepared from ((2R,3R,4S,5S)-4-(benzoyloxy)-2-(6-chloro-2-iodo-9H-purin-9-yl)-5-[(ethylamino)carbonyl]-tetrahydro-3-furanyl benzoate (Preparation 19) and 1-ethylpropylamine by the same method as Preparation 20. The title compound was obtained as a yellow foam.

¹H—NMR (400 MHz, CDCl₃)δ: 8.10–8.00 (3H, m), 7.80 (2H, m), 7.60 (1H, m), 7.50–7.40 (3H, m), 7.30 (2H, m), 6.40 (1H, m), 6.15–6.05 (2H, m), 5.75 (1H, br s), 4.90 (1H, m), 4.40 (1H, m), 4.00 (1H, m), 3.55 (1H, m), 3.35 (1H, m), 1.75 (2H, m), 1.10 (2H, m), 1.25 (6H, t).

Preparation 23

(2R,3R,4S, 5S)-4-(Benzoyloxy)-2-(6-{[(1 S)-1-benzyl-2-hydroxyethyl]amino}-2-iodo-9H-purin-9-yl)-5-[(ethylamino)carbonyl]tetrahydro-3-furanyl benzoate

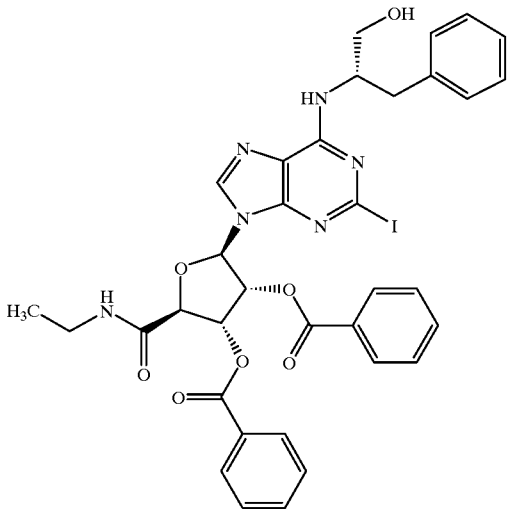

Prepared from ((2R,3R,4S,5S)-4-(benzoyloxy)-2-(6-chloro-2-iodo-9H-purin-9-yl)-5-[(ethylamino)carbonyl]-tetrahydro-3-furanyl benzoate (Preparation 19) and (2S)-2-amino-3-phenyl-1-propanol by the same method as Preparation 20. The title compound was obtained as a yellow foam.

¹H—NMR (400 MHz, CDCl₃) δ: 8.20 (1H, s), 8.05 (2H, d), 7.80 (2H, d), 7.60 (1H, m), 7.50–7.35 (4H, m), 7.30–7.20 (6H, m), 6.40 (1H, m), 6.30–6.10 (3H, m), 4.90 (1H, m), 3.90 (1H, m), 3.80 (1H, m), 4.25 (1H, br s), 3.55 (1H, m), 3.40 (1H, m), 3.10 (2H, m), 1.15 (3H, t).

Preparation 24

(2R,3R,4S,5S)-4-(Benzoyloxy)-5-[(ethylamino)carbonyl]-2-{6-[(9H-fluoren-9-ylmethyl)amino]-2-iodo-9H-purin-9-yl}tetrahydro-3-furanyl benzoate

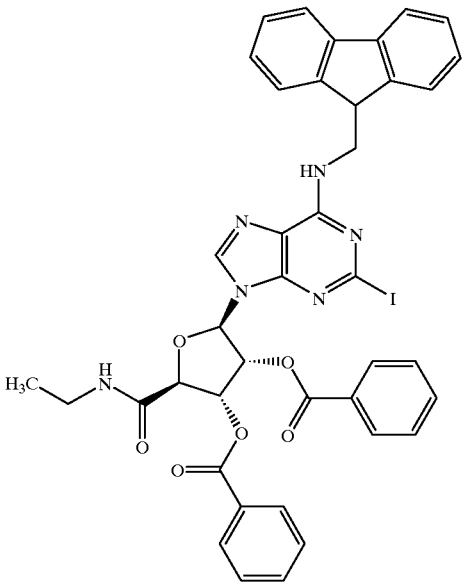

Prepared from ((2R,3R,4S,5S)-4-(benzoyloxy)-2-(6-chloro-2-iodo-9H-purin-9-yi)-5-[(ethylamino)carbonyl]-tetrahydro-3-furanyl benzoate (Preparation 19) and 9H-fluoren-9-ylmethylamine by the same method as Preparation 20. The title compound was obtained as a yellow foam.

¹H—NMR (400 MHz, CDCl₃)δ:8.05 (2H, m), 7.80 (4H, m), 7.70–7.25 (13H, m), 6.25 (1H, m), 6.15–6.05 (2H, m), 5.85 (1H, br s), 4.90 (1H, m), 4.40 (1H, m), 4.15 (1H, br s), 3.65 (1H, m), 3.50 (1H, m), 1.25 (3H, t).

LRMS: m/z [MH⁺] 821.

Preparation 25

(2R,3R,4S,5S)-4-(Benzoyloxy)-2-[6-(cyclohexylamino)-2-iodo-9H-purin-9-yl]-5-[(ethylamino)carbonyl]tetrahydro-3-furanyl benzoate

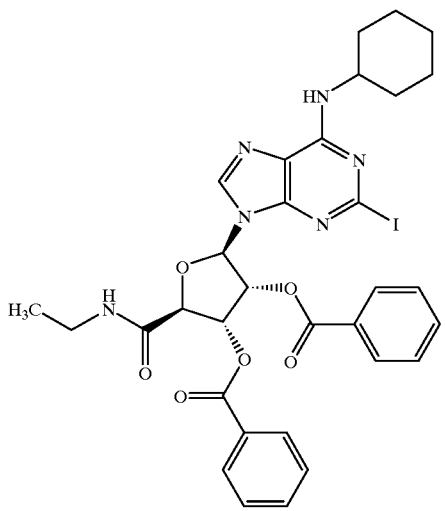

Prepared from ((2R,3R,4S,5S)-4-(benzoyloxy)-2-(6-chloro-2-iodo-9H-purin-9-yl)-5-[(ethylamino)carbonyl]-tetrahydro-3-furanyl benzoate (Preparation 19) and cyclohexylamine by the same method as Preparation 20. The title compound was obtained as a yellow foam.

¹H—NMR (400 MHz, CDCl₃) δ: 8.05 (2H, m), 7.80 (3H, m), 7.60 (1H, m), 7.50–7.40 (4H, m), 7.30–7.25 (2H, m), 6.25 (1H, m), 6.15–6.05 (2H, m), 5.70 (1H, br s), 4.90 (1H, m), 4.15 (1H, br s), 3.65 (1H, m), 3.50 (1H, m), 2.10 (2H, m), 1.80 (2H, m), 1.65 (1H, m), 1.50–1.40 (2H, m), 1.30–1.20 (6H, m).

LRMS m/z [MH⁺] 725.

Preparation 26

(2S,3S,4R,5R)-5-{6-[(2-Benzyl-3-phenylpropyl)amino]-2-iodo-9H-purin-9-yl}-N-ethyl-3,4-dihydroxytetrahydro-2-furancarboxamide

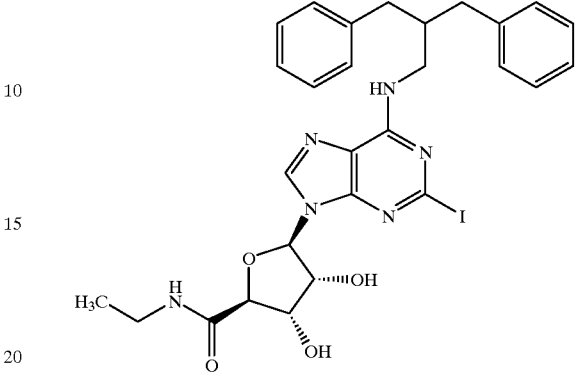

A solution of (2R,3R,4S,5S)-4-(benzoyloxy)-2-{6-[(2-benzyl-3-phenylpropyl)amino)-2-iodo-9H-purin-9-yl}-5-[(ethylamino)carbonyl]tetrahydro-3-furanyl benzoate (Preparation 20) (0.26 g, 0.31 mmol) and sodium carbonate (33 mg, 0.3 mmol) in methanol (5 ml) was stirred at room temperature for 14 hours. Solvent was removed under reduced pressure and the residue dissolved in dichloromethane:methanol (99:1 by volume; 5 ml) and filtered. Solvent was again evaporated under reduced pressure and the residue triturated with diethyl ether to afford the title compound as a beige powder (0.17 g, 86%).

¹H—NMR (400 MHz, CD₃OD) δ: 8.10 (1H, m), 7.30–7.10 (10H, m), 5.90 (1H, d), 4.70 (1H, m), 4.55–4.30 (2H, m), 3.55–3.40 (2H, m), 3.30 (1H, m), 3.00–2.90 (4H, m), 1.20 (3H, t).

LRMS: m/z [MH⁺] 629.

Preparation 27

(2S,3S,4R,5R)-5-{6-[(2,2-Diphenylethyl)amino]-2-iodo-9H-purin-9-yl}-N-ethyl-3,4-dihydroxytetrahydro-2-furancarboxamide

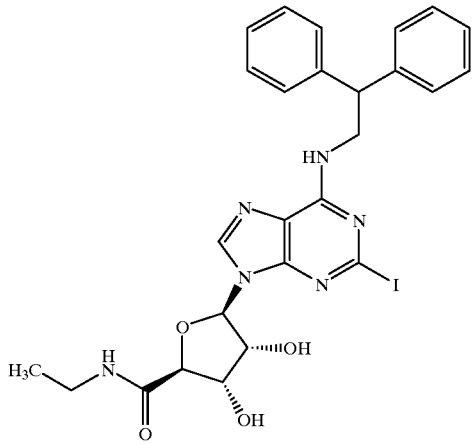

Prepared from (2R,3R,4S,5S)-4-(benzoyloxy)-2-(6-{[2,2-bis(3-phenyl)ethyl]amino}-2-iodo-9H-purin-9-yl)-5-[(ethylamino)carbonyl]tetrahydro-3-furanyl benzoate (Preparation 21) by the same method as Preparation 26. The title compound was obtained as a yellow powder.

¹H—NMR (400 MHz, CD₃OD) δ: 8.10 (1H, m), 7.35–7.15 (10H, m), 5.90 (1H, m), 4.75 (1H, m), 4.45 (1H, m), 4.40 (1H, m), 4.35 (1H, m), 4.20 (2H, m), 3.55–3.40 (2H, m), 1.20 (3H, t).

LRMS: m/z [MH⁺] 615.

Preparation 28

(2S,3S,4R,5R)-N-Ethyl-5-{6-[(1-ethylpropyl)amino]-2-iodo-9H-purin-9-yl}-3,4-dihydroxytetrahydro-2-furancarboxamide

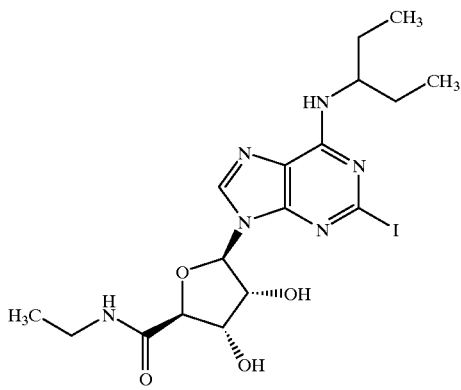

Prepared from (2R,3R,4S,5S)-4-(benzoyloxy)-5-[(ethylamino)carbonyl]-2-{6-[(1-ethylpropyl)amino]-2-iodo-9H-purin-9-yl}tetrahydro-3-furanyl benzoate (Preparation 22) by the same method as Preparation 26. The title compound was obtained as a yellow powder.

¹H—NMR (400 MHz, CDCl₃) δ: 8.10 (1H, m), 7.75 (1H, br s), 5.95 (1H, d), 5.70 (1H, m), 5.15 (1H, br s), 4.80 (1H, m), 4.60–4.45 (3H, m), 3.50 (1H, m), 3.25 (1H, m), 1.70 (2H, m), 1.50 (2H, m), 1.10 (3H, m), 0.90 (6H, t).

Preparation 29

(2S,3S,4R,5R)-5-(6-{[(1 S)-1-Benzyl-2-hydroxyethyl]amino}-2-iodo-9H-purin-9-yl)-N-ethyl-3,4-dihydroxytetrahydro-2-furancarboxamide

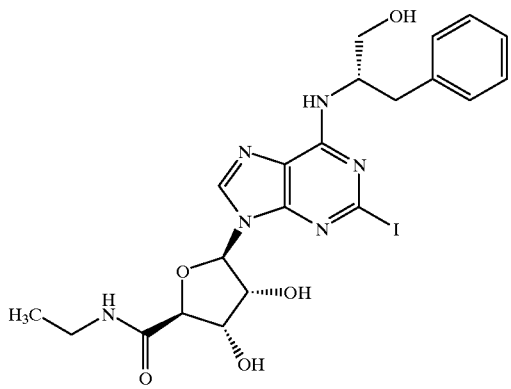

Prepared from (2R,3R,4S,5S)-4-(benzoyloxy)-2-(6-{[(1S)-1-benzyl-2-hydroxyethyl]amino}-2-iodo-9H-purin-9-yl)-5-[(ethylamino)carbonyl]tetrahydro-3-furanyl benzoate (Preparation 23) by the same method as Preparation 26. The title compound was obtained as a yellow powder.

¹H—NMR (400 MHz, CDCl₃)δ: 8.10 (1H, br s), 7.50–7.10 (5H, m), 6.65 (1H, br s), 5.95 (1H, m), 4.80 (1H, m), 4.60–4.40 (2H, m), 3.70 (1H, m), 3.50 (1H, m), 3.35 (1H, m), 3.10 (2H, m), 1.15 (3H, t).

Preparation 30

(2 S,3S,4R,5R)-N-Ethyl-5-{6-[(9H-fluoren-9-ylmethy)amino]-2-iodo-9H-purin-9-yl}-3,4-dihydroxytetrahydro-2-furancarboxamide

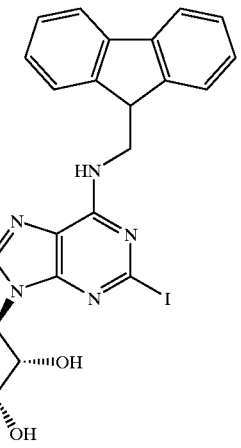

Prepared from (2R,3R,4S,5S)-4-(benzoyloxy)-5-[(ethylamino)carbonyl]-2-{6-[(9H-fluoren-9-ylmethyl)amino]-2-iodo-9H-purin-9-yl}tetrahydro-3-furanyl benzoate (Preparation 24) by the same method as Preparation 26. The title compound was obtained as a yellow powder.

¹H—NMR (400 MHz, CD₃OD) δ: 8.10 (1H, s), 7.80 (2H, d), 7.65 (2H, m), 7.40–7.20 (4H, m), 5.90 (1H, d), 4.75 (1H, m), 4.40 (1H, s), 4.35 (2H, br s), 4.10 (2H, m), 3.45 (2H, m), 1.20 (3H, t).

LRMS: m/z [MH⁺] 613.

Preparation 31

(2S,3S,4R,5R)-5-[6-(Cyclohexylamino)-2-iodo-9H-purin-9-yl]-N-ethyl-3,4-dihydroxytetrahydro-2-furancarboxamide

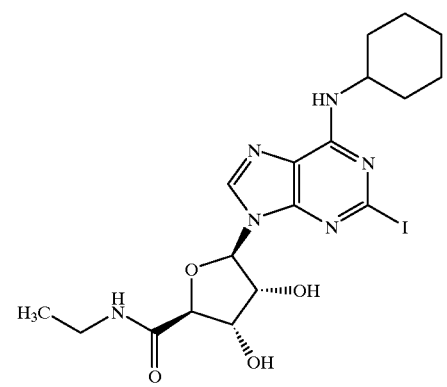

Prepared from (2R,3R,4S, 5S)-4-(benzoyloxy)-2-[6-(cyclohexylamino)-2-iodo-9H-purin -9-yl]-5-[(ethylamino)carbonyl]tetrahydro-3-furanyl benzoate (Preparation 25) by the same method as Preparation 26. The title compound was obtained as a yellow powder.

$^1$H—NMR (400 MHz, CD$_3$OD) δ: 8.15 (1H, s), 5.90 (1H, d), 4.70 (1H, m), 4.40 (1H, s), 4.30 (1H, d), 4.05 (1H, br s), 3.50–3.40 (2H, m), 2.00 (2H, m), 1.80 (2H, m), 1.60 (1H, m), 1.50–1.20 (6H, m), 1.15 (3H, t).

LRMS: m/z [MH$^+$] 517.

What is claimed is:

1. A compound of the formula:

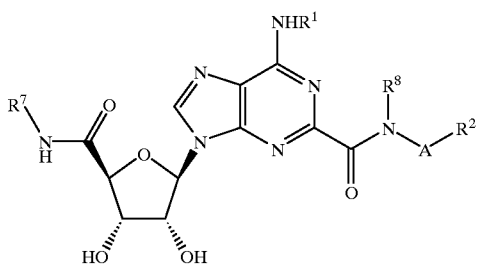

(I)

or a pharmaceutically acceptable salt or solvate thereof,
wherein R$^1$ is hydrogen, C$_1$–C$_6$ alkyl or C$_3$–C$_7$ cycloalkyl, each optionally substituted by 1 or 2 substituents each independently selected from hydroxyl, fluorenyl, phenyl and naphthyl, said phenyl and naphthyl being optionally substituted by C$_1$–C$_6$ alkyl, C$_1$–C$_6$ alkoxy, halo or cyano;
A is a bond or C$_1$–C$_6$ alkylene;
R$^2$ is (i) hydrogen, C$_1$–C$_6$ alkyl, C$_3$–C$_7$ cycloalkyl, phenyl or naphthyl, said C$_3$–C$_7$ cycloalkyl, phenyl and naphthyl being optionally substituted by C$_1$–C$_6$ alkyl, phenyl, C$_1$–C$_6$ alkoxy-(C$_1$–C$_6$)-alkyl, amino-(C$_1$–C$_6$)-alkyl, fluoro-(C$_1$–C$_6$)-alkyl, fluoro-(C$_1$–C$_6$)-alkoxy, C$_2$–C$_5$ alkanoyl, halo, —OR$^3$, cyano, —COOR$^3$, C$_3$–C$_7$ cycloalkyl, —S(O)$_m$R$^4$, —NR$^3$R$^3$, —SO$_2$NR$^3$R$^3$, —CONR$^3$R$^3$, —NR$^3$COR$^4$ or —NR$^3$SO$_2$R$^4$, with the proviso that R$^2$ is not hydrogen when A is a bond, or(ii) when A is C$_2$–C$_6$ alkylene, —NR$^3$R$^3$, —OR$^3$, —COOR$^3$, —OCOR$^4$, —SO$_2$R$^4$, —CN, —SO$_2$NR$^3$R$^4$, —NR$^3$SO$_2$R$^4$, —NR$^3$SO$_2$R$^4$ or —CONR$^3$R$^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, C$_1$–C$_6$ alkoxy-(C$_1$–C$_6$)-alkyl, amino-(C$_1$–C$_6$)-alkyl, fluoro-(C$_1$–C$_6$)-alkyl, fluoro-(C$_1$–C$_6$)-alkoxy, fluoro-(C$_2$–C$_5$)-alkanoyl, halo, cyano, -OR$^5$,R$^6$, —COR$^5$, —NR$^5$R$^5$, —COOR$^5$, —S(O)$_m$R$^6$, —SO$_2$N$^5$R$^5$R$^5$, —CONR$^5$R$^5$, —NR$^5$SO$_2$R$^6$ or —NR$^5$COR$^6$ and optionally N-substituted by C$_1$–C$_6$ alkoxy-(C$_1$–C$_6$)-alkyl, amino-(C$_2$–C$_6$)-alkyl, fluoro-(C$_1$–C$_6$)-alkyl, fluoro-(C$_2$–C$_5$)-alkanoyl, R$^6$, —COR$^5$, —COOR$^6$, —SO$_2$R$^6$, —SO$_2$NR$^5$R$^5$ or —CONR$^5$R$^5$, or (iv) when A is C$_2$–C$_6$ alkylene, N-linked azetidinyl, pyrrolidinyl, morpholinyl, tetrahydroisoquinolinyl, piperidinyl or piperazinyl, each being optionally C-substituted by C$_1$–C$_6$ alkyl, phenyl, C$_1$–C$_6$ alkoxy-(C$_1$–C$_6$)-alkyl, amino-(C$_1$–C$_6$)-alkyl, fluoro-(C$_1$–C$_6$)-alkyl, fluoro-(C$_1$–C$_6$)-alkoxy, C$_2$–C$_5$ alkanoyl, halo, —OR$^3$, cyano, —COOR$^3$, C$_3$–C$_7$ cycloalkyl, —S(O)$_m$R$^4$, —NR$^3$R$^3$, —SO$_2$NR$^3$R$^3$, —CONR$^3$R$^3$, —NR$^3$COR$^4$ or —NR$^3$SO$_2$R$^4$ and said piperazinyl being optionally N-substituted by C$_1$–C$_6$ alkyl, phenyl, C$_1$–C$_6$ alkoxy-(C$_1$–C$_6$)-alkyl, amino-(C$_2$–C$_6$)-alkyl, fluoro-(C$_1$–C$_6$)-alkyl, C$_2$–C$_5$ alkanoyl, —COOR$^4$, C$_3$–C$_7$ cycloalkyl, —SO$_2$R$^4$, —SO$_2$NR$^3$R$^3$ or —CONR$^3$R$^3$;
each R$^3$ is independently selected from H, C$_1$–C$_6$ alkyl, phenyl or pyridinyl;
R$^4$ is C$_1$–C$_6$ alkyl or phenyl;
R$^5$ is H, C$_1$–C$_6$ alkyl, C$_3$–C$_7$ cycloalkyl, phenyl, naphthyl or het;
R$^6$ is C$_1$–C$_6$ alkyl, C$_3$–C$_7$ cycloalkyl, phenyl, naphthyl or het;
m is 0, 1 or 2;
R$^7$ is hydrogen, C$_1$–C$_6$ alkyl, C$_3$–C$_7$ cycloalkyl, phenyl, naphthyl, azetidin-3-yl, pyrrolidin-3-yl, piperidin-3-yl, piperidin-4-yl or het, said azetidin-3-yl, pyrrolidin-3-yl, piperidin-3-yl and piperidin-4-yl being optionally substituted by C$_1$–C$_6$ alkyl;
R$^8$ is H or C$_1$–C$_6$ alkyl; and
"het", used in the definitions of R$^5$, R$^6$ and R$^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each being optionally substituted by C$_1$–C$_6$ alkyl, C$_1$–C$_6$ alkoxy, cyano or halo.

2. A compound as claimed in claim 1, wherein R$^1$ is selected from 2,2-diphenylethyl, cyclohexyl,1-ethylpropyl, 1-benzyl-2-hydroxyethyl, 9H-fluoren-9-ylmethyl, and 1-benzyl-2-phenylethyl.

3. A compound as claimed in claim 1, wherein R$^1$ is selected from phenyl, pyrrolidinyl, pyridinyl, optionally substituted piperidinyl, optionally substituted piperazinyl, optionally substituted imidazolyl, morpholinyl, tetrahydroisoquinolyl, C$_1$–C$_6$ alkylamino, di- C$_1$–C$_6$ alkylamino, pyridinylamino and —NR$^3$SO$_2$R$^4$.

4. A compound as claimed in claim 1, wherein R$^7$ is ethyl or n-propyl.

5. A compound as claimed in claim 1, wherein R$^8$ is H.

6. A compound as claimed in claim 1 which is a member selected from the group consisting of:

6-[(2,2-diphenylethyl)amino]-9-{(2R,3R,4S,5S)-5-[(ethylamino)carbonyl]-3,4- dihydroxytetrahydro-2-furanyl}-N-(2-pyridinylmethyl)-9H-purine-2-carboxamide;

N-benzyl-6-[(2,2-diphenylethyl)amino]-9-{(2R,3R,4S, 5S)-5-(ethylamino)carbonyl]-3,4-dihydroxytetrahydro-2-furanyl}-9H-purine-2- carboxamide;

6-[(2,2-diphenylethyl)amino]-9-{(2R,3R,4S,5S)-5-[(ethylamino)carbonyl]-3,4- dihydroxytetrahydro-2-furanyl}-N-(2-phenylethyl)-9H-purine-2-carboxamide;

N-[2-(dimethylamino)ethyl]-6-[(2,2-diphenylethyl)amino]-9-{(2R,3R,4S,5S)-5- [(ethylamino)carbonyl]-3,4-dihydroxytetrahydro-2-furanyl}-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[3-(1-pyrrolidinyl)propyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[2-(2-pyridinyl)ethyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[2-(4-morpholinyl)ethyl]-9H-purine-2-carboxamide;

9-{(2R,3R,4S,5S)-5-[(ethylamino)carbonyl]-3,4-dihydroxytetrahydro-2-furanyl}-6-[(1-ethylpropyl)amino]-N-[2-(1-piperidinyl)ethyl]-9H-purine-2-carboxamide;

6-{[(1S)-1-benzyl-2-hydroxyethyl]amino}-9-{(2R,3R,4S,5S)-5-[(ethylamino)carbonyl]-3,4-dihydroxytetrahydro-2-furanyl}-N-[2-(1-piperidinyl)ethyl]-9H-purine-2-carboxamide;

6-[(2,2-diphenylethyl)amino]-9-{(2R,3R,4S,5S)-5-[(ethylamino)carbonyl]-3,4-dihydroxytetrahydro-2-furanyl}-N-[2-(4-isopropyl-1-piperidinyl)ethyl]-9H-purine-2-carboxamide;

N-[2-(3,4-dihydro-2(1H)-isoquinolinyl)ethyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-(4-piperidinylmethyl)-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[4-(1-piperidinyl)butyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[3-(isopropylamino)propyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[3-(2-pyridinylamino)propyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-{3-[methyl(phenylsulfonyl)amino]propyl}-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-{3-[methyl(methylsulfonyl)amino]propyl}-9H-purine-2-carboxamide;

9-{(2R,3R,4S,5S)-5-[(ethylamino)carbonyl]-3,4-dihydroxytetrahydro-2-furanyl}-6-[(9H-fluoren-9-ylmethyl)amino]-N-[2-(1-piperidinyl)ethyl]-9H-purine-2-carboxamide;

N-[3-(diethylamino)propyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[3-(4-morpholinyl)propyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[3-(methylamino)propyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[2-(5-methyl-1H-imidazol-4-yl)ethyl]-9H-purine-2-carboxamide;

N-[4-(dimethylamino)butyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[3-(4-methyl-1-piperazinyl)propyl]-9H-purine-2-carboxamide;

N-[3-(dimethylamino)propyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide;

6-[(1-benzyl-2-phenylethyl)amino]-9-{(2R,3R,4S,5S)-5-[(ethylamino)carbonyl]-3,4- dihydroxytetrahydro-2-furanyl}-N-[2-(1-piperidinyl)ethyl]-9H-purine-2-carboxamide;

9-{(2R,3R,4S,5S)-3,4-dihydroxy-5-[(propylamino)carbonyl]tetrahydro-2-furanyl}-6-[(2,2-diphenylethyl)amino]-N-[2-(1-piperidinyl)ethyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[2-(1-isopropyl-4-piperidinyl)ethyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[2-(4-methyl-1-piperidinyl)ethyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[2-(4-methoxy-1-piperidinyl)ethyl]-9H-purine-2-carboxamide;

6-[(2,2-diphenylethyl)amino]-9-{(2R,3R,4S,5S)-5-[(ethylamino)carbonyl]-3,4- dihydroxytetrahydro-2-furanyl}-N-[(1-methyl-1H-imidazol-4-yl)methyl]-9H-purine-2-carboxamide; and, 6-(cyclohexylamino)-9-{(2R,3R,4S,5S)-5-[(ethylamino)carbonyl]-3,4-dihydroxytetrahydro-2-furanyl}-N-[2-(1-piperidinyl)ethyl]-9H-purine-2-carboxamide, or a pharmaceutically acceptable salt or solvate thereof.

7. A pharmaceutical composition including a compound of the formula (I) as defined in claim 1, or a pharmaceutically acceptable salt or solvate thereof, together with a pharmaceutically acceptable excipient, diluent or carrier.

8. A method of treatment of a mammal for treating a disease for which a A2a receptor agonist is indicated, comprising treating said mammal with an effective amount of a compound of the formula (I) as defined in claim 1 or with a pharmaceutically acceptable salt, solvate or composition thereof.

9. A method as claimed in claim 8, wherein the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

10. A compound of the formula (II), (III), (XI), (XIII), (XIV), (XV), (XVI), (XIX), (XIXb), (XIXc), or (XIXd):

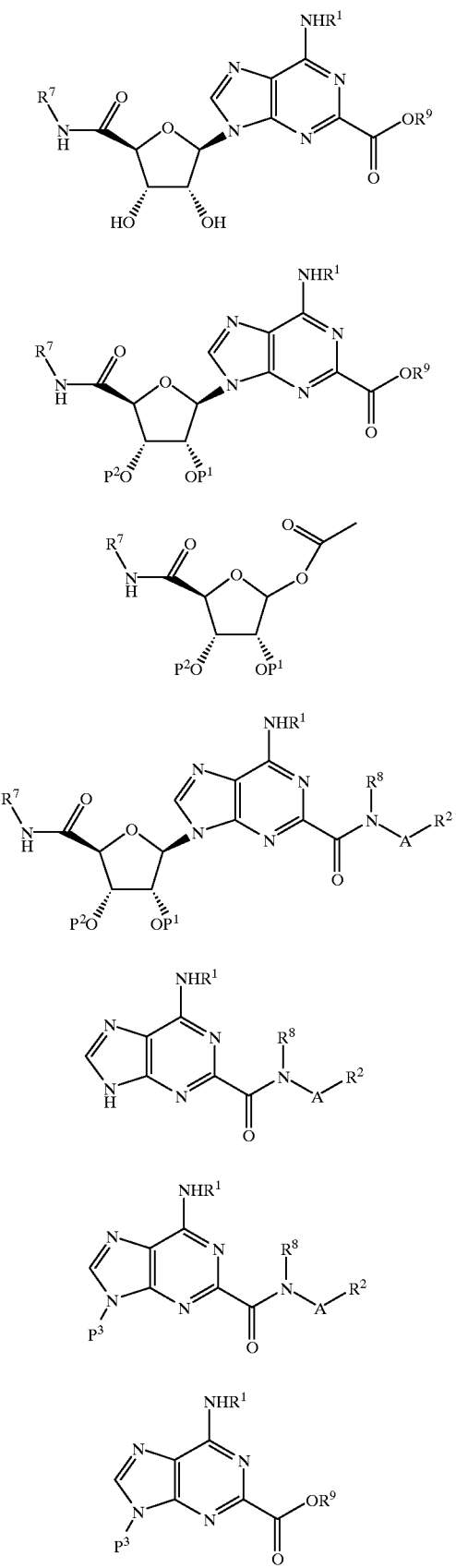
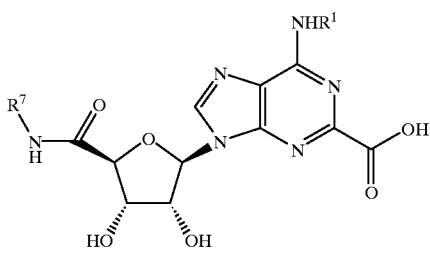
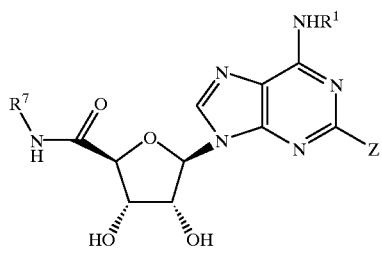
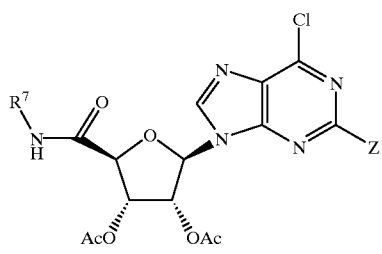
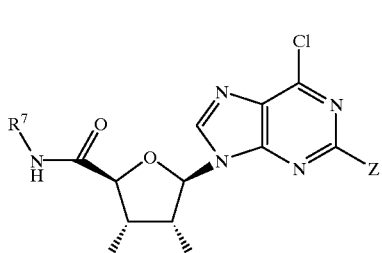
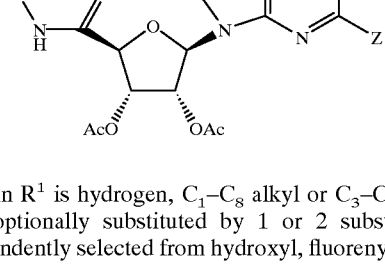
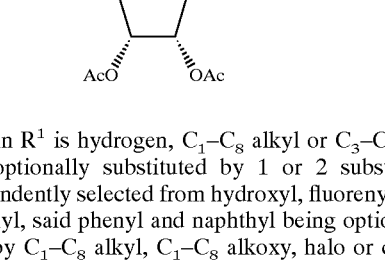
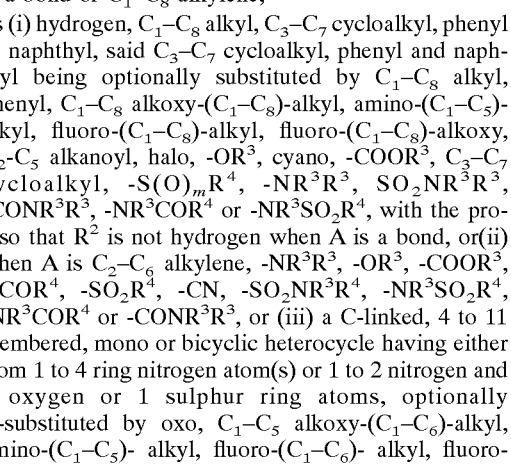

wherein $R^1$ is hydrogen, $C_1$–$C_8$ alkyl or $C_3$–$C_7$ cycloalkyl, each optionally substituted by 1 or 2 substituents each independently selected from hydroxyl, fluorenyl, phenyl and naphthyl, said phenyl and naphthyl being optionally substituted by $C_1$–$C_8$ alkyl, $C_1$–$C_8$ alkoxy, halo or cyano;

A is a bond or $C_1$–$C_8$ alkylene;

$R^2$ is (i) hydrogen, $C_1$–$C_8$ alkyl, $C_3$–$C_7$ cycloalkyl, phenyl or naphthyl, said $C_3$–$C_7$ cycloalkyl, phenyl and naphthyl being optionally substituted by $C_1$–$C_8$ alkyl, phenyl, $C_1$–$C_8$ alkoxy-($C_1$–$C_8$)-alkyl, amino-($C_1$–$C_5$)-alkyl, fluoro-($C_1$–$C_8$)-alkyl, fluoro-($C_1$–$C_8$)-alkoxy, $C_2$-$C_5$ alkanoyl, halo, -$OR^3$, cyano, -$COOR^3$, $C_3$–$C_7$ cycloalkyl, -$S(O)_mR^4$, -$NR^3R^3$, $SO_2NR^3R^3$, -$CONR^3R^3$, -$NR^3COR^4$ or -$NR^3SO_2R^4$, with the proviso that $R^2$ is not hydrogen when A is a bond, or (ii) when A is $C_2$–$C_6$ alkylene, -$NR^3R^3$, -$OR^3$, -$COOR^3$, $OCOR^4$, -$SO_2R^4$, -$CN$, -$SO_2NR^3R^4$, -$NR^3SO_2R^4$, -$NR^3COR^4$ or -$CONR^3R^3$, or (iii) a C-linked, 4 to 11 membered, mono or bicyclic heterocycle having either from 1 to 4 ring nitrogen atom(s) or 1 to 2 nitrogen and 1 oxygen or 1 sulphur ring atoms, optionally C-substituted by oxo, $C_1$–$C_5$ alkoxy-($C_1$–$C_6$)-alkyl, amino-($C_1$–$C_5$)- alkyl, fluoro-($C_1$–$C_6$)- alkyl, fluoro- ($C_1$–$C_6$)-alkoxy, fluoro-($C_2$–$C_5$)-alkanoyl, halo, cyano, -OR$^5$, R$^5$, -COR$^5$, -NR$^5$R$^5$, -COOR$^5$, -S(O)$_m$R$^6$, -SO$_2$NR$^5$%$^5$, -CONR$^5$R$^5$, -NR$^5$SO$_2$R$^6$ or -NR$^5$COR$^6$ and optionally N-substituted by $C_1$–$C_5$ alkoxy-($C_1$–$C_6$)-alkoxy, amino-($C_2$–$C_6$)-alkyl, fluoro-($C_1$–$C_6$)-alkyl, fluoro-($C_2$–$C_5$)-alkanoyl, R$^6$, -COR$^5$, -COOR$^6$, -SO$_2$R$^6$, -SO$_2$NR$^5$R$^5$ or -CONR$^5$R$^5$or (iv) when a is $C_2$–$C_5$ alkylene, N-linked azetidinyl, pyrrolidinyl, morpholinyl, tetrahydroisoquinolinyl, piperidinyl or piperazinyl, each being optionally C-substituted by $C_1$–$C_6$ alkyl, phenyl, $C_1$–$C_6$ alkoxy-($C_1$–$C_6$)-alkyl, amino-($C_1$–$C_6$)-alkyl, fluoro-($C_1$–$C_6$)- alkyl, fluoro-($C_1$–$C_6$)-alkoxy, $C_2$–$C_5$ alkanoyl, halo, -OR$^3$, cyano, -COOR$^3$, $C_3$–$C_7$ cycloalkyl, -S(O)$_m$R$^4$, -NR$^3$R$^3$, -SO$_2$NR$^3$R$^3$, -CONR$^3$R$^3$, -NR$^3$COR$^4$ or -NR$^3$SO$_2$R$^4$ and said piperazinyl being optionally N-substituted by $C_1$–$C_6$ alkyl, phenyl, $C_1$–$C_6$ alkoxy-($C_1$–$C_6$)-alkyl, amino-($C_2$–$C_8$)-alkyl, fluoro-($C_1$–$C_6$)-alkyl, $C_2$–$C_5$ alkanoyl, -COOR$^4$, $C_3$–$C_7$ cycloalkyl, -SO$_2$R$^4$, -SO$_2$NR$^3$R$^3$ or -CONR$^3$R$^3$;

each R$^3$ is independently selected from H, $C_1$–$C_6$ alkyl, phenyl pr pyridieyl;

R$^4$ is $C_1$–$C_6$ alkyl or phenyl;

R$^5$ is H, $C_1$–$C_6$ alkyl, $C_3$—$C_7$ cycloalkyl, phenyl, naphthyl or het;

R$^6$ is $C_1$–$C_6$ alkyl. $C_3$–$C_7$ cycloalkyl, phenyl, naphthyl or het;

m is 0, 1 or 2;

R$^7$ is hydrogen, $C_1$–$C_5$ alkyl, $C_3$–$C_7$ cycloalkyl, phenyl, naphthyl, azetidin-3-yo, pyrrolidin-3-yl, piperidin-3-yl, piperidin-4-yl or het, said azetidin-3-yl, pyrrolidin-3-yl, piperidin-3-yl and piperidin-4-yl being optionally substituted by $C_1$–$C_6$ alkyl;

R$^5$ is H or $C_1$–$C_8$ alkyl; and

"het", used in the definitions of R$^5$, R$^6$ and R$^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinolinyl, each being optionally substituted by $C_1$–$C_6$ R$^9$ is $C_1$–$C_4$ alkyl; P$^1$, P$^2$, and P$^3$ are protecting groups; and Z is a leaving group.

11. A method according to claim 8 wherein said mammal being treated is a human being.

* * * * *